(12) United States Patent
Sokolovskyy et al.

(10) Patent No.: US 12,115,339 B2
(45) Date of Patent: Oct. 15, 2024

(54) INTERACTIVE GUIDANCE FOR MEDICAL DEVICES

(71) Applicant: MEDTRONIC MINIMED, INC., Northridge, CA (US)

(72) Inventors: Dmytro Y. Sokolovskyy, Moorpark, CA (US); Shawn A. Coumbe, Los Angeles, CA (US); Maria Diana Miller, Santa Rosa Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 17/930,391

(22) Filed: Sep. 7, 2022

(65) Prior Publication Data
US 2023/0005588 A1    Jan. 5, 2023

Related U.S. Application Data

(63) Continuation of application No. 15/362,642, filed on Nov. 28, 2016, now abandoned.

(51) Int. Cl.
*G16H 40/63* (2018.01)
*A61M 5/142* (2006.01)
(Continued)

(52) U.S. Cl.
CPC ............ *A61M 5/142* (2013.01); *G16H 40/63* (2018.01); *A61M 2005/14208* (2013.01);
(Continued)

(58) Field of Classification Search
None
See application file for complete search history.

(56) References Cited

U.S. PATENT DOCUMENTS

| 3,631,847 A | 1/1972 | Hobbs |
|---|---|---|
| 4,212,738 A | 7/1980 | Henne |

(Continued)

FOREIGN PATENT DOCUMENTS

| DE | 4329229 A1 | 3/1995 |
|---|---|---|
| EP | 0319268 B1 | 1/1997 |

(Continued)

OTHER PUBLICATIONS

Harte RP, Glynn LG, Broderick BJ, Rodriguez-Molinero A, Baker PM, McGuiness B, O'Sullivan L, Diaz M, Quinlan LR, ÓLaighin G. "Human centred design considerations for connected health devices for the older adult." J Pers Med. Jun. 4, 2014;4(2):245-81. (Year: 2014).*

(Continued)

*Primary Examiner* — Rachel L. Porter
(74) *Attorney, Agent, or Firm* — Fortem IP LLP

(57) ABSTRACT

Disclosed herein are techniques related to interactive guidance for medical devices. The techniques may involve identifying, by an application executing on a computing device, a user objective with respect to a medical device communicatively coupled to the computing device. The techniques may further involve obtaining state information for a current state of a graphical user interface of the medical device. The techniques may also involve generating, based on the current state of the graphical user interface, a guidance user interface comprising an ordered sequence of actuations of user input elements to achieve the identified user objective. Additionally, the techniques may involve obtaining updated state information for an updated state of the graphical user interface. The updated state information may be obtained responsive to an actuation of a user input element. Furthermore, the techniques may involve dynami- (Continued)

cally updating the guidance user interface based on the updated state information.

20 Claims, 15 Drawing Sheets

(51) Int. Cl.
 *A61M 5/172* (2006.01)
 *G16H 20/17* (2018.01)
(52) U.S. Cl.
 CPC ............ *A61M 5/172* (2013.01); *A61M 5/1723* (2013.01); *A61M 2205/3303* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2230/201* (2013.01); *G16H 20/17* (2018.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell et al. |
| 4,395,259 A | 7/1983 | Prestele et al. |
| 4,433,072 A | 2/1984 | Pusineri et al. |
| 4,443,218 A | 4/1984 | Decant et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen |
| 4,781,798 A | 11/1988 | Gough |
| 4,803,625 A | 2/1989 | Fu et al. |
| 4,809,697 A | 3/1989 | Causey et al. |
| 4,826,810 A | 5/1989 | Aoki |
| 4,871,351 A | 10/1989 | Feingold |
| 4,898,578 A | 2/1990 | Rubalcaba |
| 4,982,872 A | 1/1991 | Avery |
| 4,998,578 A | 3/1991 | Dwivedi et al. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist et al. |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes et al. |
| 5,376,070 A | 12/1994 | Purvis et al. |
| 5,390,671 A | 2/1995 | Lord et al. |
| 5,391,250 A | 2/1995 | Cheney et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |

(56) References Cited

U.S. PATENT DOCUMENTS

| | | |
|---|---|---|
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | Delahuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Chen et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,560,741 B1 | 5/2003 | Sardi et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,402,153 B2 | 7/2008 | Steil et al. |
| 7,621,893 B2 | 11/2009 | Moberg et al. |
| 8,474,332 B2 | 7/2013 | Bente et al. |
| 8,674,288 B2 | 3/2014 | Hanson et al. |
| 2001/0044731 A1 | 11/2001 | Coffman et al. |
| 2002/0013518 A1 | 1/2002 | West et al. |
| 2002/0055857 A1 | 5/2002 | Mault |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0158193 A1* | 8/2004 | Bui ................. A61M 5/172 |
| | | 128/DIG. 13 |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon |
| 2005/0055244 A1* | 3/2005 | Mullan ............. G16H 40/63 |
| | | 705/2 |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0036750 A1* | 2/2009 | Weinstein ......... G16H 40/67 |
| | | 600/300 |
| 2009/0081951 A1 | 3/2009 | Erdmann et al. |
| 2009/0082635 A1 | 3/2009 | Baldus et al. |
| 2009/0088197 A1* | 4/2009 | Stewart ............ H04M 1/72412 |
| | | 455/550.1 |
| 2012/0174022 A1* | 7/2012 | Sandhu ............. G16H 40/63 |
| | | 715/781 |
| 2014/0210600 A1 | 7/2014 | Lautenschlaeger et al. |
| 2015/0057634 A1 | 2/2015 | Mastrototaro et al. |
| 2015/0057807 A1 | 2/2015 | Mastrototaro et al. |
| 2015/0151050 A1* | 6/2015 | Estes ................. A61M 5/172 |
| | | 604/151 |
| 2018/0150614 A1 | 5/2018 | Sokolovskyy et al. |
| 2021/0146041 A1* | 5/2021 | Rosinko ............ G16H 40/63 |

FOREIGN PATENT DOCUMENTS

| | | | |
|---|---|---|---|
| EP | 0806738 A1 | 11/1997 | |
| EP | 0880936 A2 | 12/1998 | |
| EP | 1338295 A1 | 8/2003 | |
| EP | 1631036 A2 | 3/2006 | |
| GB | 2218831 A | 11/1989 | |
| WO | 9620745 A1 | 7/1996 | |
| WO | 9636389 A1 | 11/1996 | |
| WO | 9637246 A1 | 11/1996 | |
| WO | 9721456 A1 | 6/1997 | |
| WO | 9820439 A1 | 5/1998 | |
| WO | 9824358 A2 | 6/1998 | |
| WO | 9842407 A1 | 10/1998 | |
| WO | 9849659 A2 | 11/1998 | |
| WO | 9859487 A1 | 12/1998 | |
| WO | 9908183 A1 | 2/1999 | |
| WO | 9910801 A1 | 3/1999 | |
| WO | 9918532 A1 | 4/1999 | |
| WO | 9922236 A1 | 5/1999 | |
| WO | 0010628 A2 | 3/2000 | |
| WO | 0019887 A1 | 4/2000 | |
| WO | WO-0048112 A2 * | 8/2000 | ............ A61M 5/172 |
| WO | 02058537 A2 | 8/2002 | |
| WO | 03001329 A2 | 1/2003 | |
| WO | 03094090 A2 | 11/2003 | |
| WO | 2005065538 A2 | 7/2005 | |

(56) References Cited

FOREIGN PATENT DOCUMENTS

OTHER PUBLICATIONS

Koudelka, et al., "In-vivo Behaviour of Hypodermically Implanted Microfabricated Glucose Sensors", Biosensors & Bioelectronics 6, 1991, pp. 31-36.
Koudelka, et al., "Planar Amperometric Enzyme-Based Glucose Microelectrode", Sensors & Actuators, 18, 1989, pp. 157-165.
Kulkarni, et al., Carbohydrate Counting A Primer for Insulin Pump Users to Zero in on GoodControl. MiniMed Inc. (1999).
Marcus, et al., "Insulin Pump Therapy Acceptable Alternative to Injection Therapy", Postgraduate Medicine, vol. 99, No. 3, pp. 125-142. (1996).
Mastrototaro, John J., et al., "An electroenzymatic glucose sensor fabricated on a flexible substrate", Sensors & Actuators, B. 5, 1991, pp. 139-144.
Mastrototaro, John J., et al., "An Electroenzymatic Sensor Capable of 72 Hour Continuous Monitoring of Subcutaneous Glucose", 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors", IEEE Transactions on Biomedical Engineering, Vo. 35, No. 7, Jul. 1988, pp. 526-532.
Monroe, et al., "Novel Implantable Glucose Sensors", ACL, Dec. 1989, pp. 8-16.
Morff, Robert J., et al., "Microfabrication of Reproducible, Economical, Electroenzymatic Glucose Sensors", Annuaal International Conference of teh IEEE Engineering in Medicine and Biology Society, Vo. 12, No. 2, 1990, pp. 483-484.
Moussy, Francis, "Performance of Subcutaneously Implanted Needle-Type Glucose Sensors Employing a Novel Trilayer Coating", Analytical Chemistry, vol. 65, No. 15, Aug. 1, 1993, pp. 2072-2077.
Nakamoto, et al., "A Lift-Off Method for Patterning Enzyme-Immobilized Membranes in Multi-Biosensors", Sensors and Actuators 13, 1988, pp. 165-172.
Nishida, Kenro, et al., "Clinical applications of teh wearable artifical endocrine pancreas with the newly designed heedle-type glucose sensor", Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate", Medical Progress Through Technology, vol. 21, 1995, pp. 91-103.
Poitout, et al., "A glucose monitoring system for on line estimation oin man of blood glucose concentration using a miniaturized glucose sensor implanted in the subcutaneous tissue adn a wearable control unit", Diabetologia, vol. 36, 1991, pp. 658-663.
Reach, "A Method for Evaluating in vivo the Functional Characteristics of Glucose Sensors", Biosensors 2,1986, pp. 211-220.
Reed, et al., Voice of the Diabetic, vol. 11, No. 3, pp. 1-38. (1996).
Shaw, et al., "In vitro testing of a simply constructed, highly stable glucose sensor suitable for implantation in diabetic patients", Biosensors & Bioelectronics 6, 1991, pp. 401-406.
Shichiri, "A Needle-Type Glucose Sensor—A Valuable Tool Not Only For a Self-Blood Glucose Monitoring but for a Wearable Artifiical Pancreas", Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor", Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response", Diabetes, vol. 33, Dec. 1984, pp. 1200-1202.
Shichiri, Motoaki, et al., "Glycaemic Control in a Pacreatectomized Dogs with a Wearable Artificial Endocrine Pancreas", Diabetologia, vol. 24, 1983, pp. 179-184.
Shichiri, et al., "Membrane design for extending the long-life of an implantable glucose sensor", Nutr. Metab., vol. 2, No. 4, 1989, pp. 309-313.
Shichiri, et al., "n Vivo Characteristics of Needle-Type Glucose Sensor—Measurements of Subcutaneous Glucose Concentrations in Human Volunteers", Hormone and Metabolic Research, Supplement Series vol. No. 20, 1988, pp. 17-20.
Shichiri, Motoaki, et al., "Normalization of the Paradoxic Secretion of Glucagon in Diabetes Who Were Controlled by the Artificial Beta Cell", Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals", Diabetes Care, vol. 9, No. 3, May-Jun. 1986, pp. 298-301.
Shichiri, Motoaki, et al., "The Wearable Artificial Endocrine Pancreas with a Needle-Type Glucose Sensor: Perfect Glycemic Control in Ambulatory Diabetes", Acta Paediatr Jpn 1984, vol. 26, pp. 359-370.
Shichiri, Motoaki, et al., "Wearable Artificial Endocrine Pancreas with Needle-Type Glucose Sensor", The Lancet, Nov. 20, 1982, pp. 1129-1131.
Shinkai, Seiji, "Molecular Recognition of Mono- and Disaccharides by Phenylboronic Acids in Solvent Extraction and as a Monolayer", J. Chem. Soc., Chem. Commun., 1991, pp. 1039-1041.
Shults, Mark C., "A Telemetry-Instrumentation System for Monitoring Multiple Subcutaneously Implanted Glucose Sensors", IEEE Transactions on Biomedical Engineering, vol. 41, No. 10, Oct. 1994, pp. 937-942.
Skyler, et al., Continuous Subcutaneous Insulin Infusion [CSII] With External Devices: Current Status. Update in Drug Delivery Systems, Chapter 13, pp. 163-183. Futura Publishing Company. (1989).
Skyler, et al., The Insulin Pump Therapy Book Insights from the Experts. MiniMed Technologies. (1995).
Sternberg, Robert, et al., "Study and Development of Multilayer Needle-type Enzyme-based Glucose Microsensors", Biosensors, vol. 4, 1988, pp. 27-40.
Strowig, "Initiation and Management of Insulin Pump Therapy", The Diabetes Educator, vol. 19, No. 1, pp. 50-60. (1993).
Tamiya, et al., "Micro Glucose Sensors using Electron Mediators Immobilized on a Polypyrrole-Modified Electrode", Sensors and Actuators, vol. 18, 1989, pp. 297-307.
Tsukagoshi, Kazuhiko, et al., "Specific Complexation with Mono- and Disaccharides that can be Detected by Circular Dichroism", J. Org. Chem., vol. 56, 1991, pp. 4089-4091.
Ubran, et al., "Miniaturized thin-film biosensors using covalently immobilized glucose oxidase", Biosensors & Bioelectronics, vol. 6, 1991, pp. 555-562.
Urban, et al., "Miniaturized multi-enzyme biosensors integrated with pH sensors on flexible polymer carriers for in vivo applciations,", Biosensors & Bioelectronics, vol. 7, 1992, pp. 733-739.
Velho, et al., "In vivo calibration of a subcutaneous glucose sensor for determination of subcutaneous glucose kinetics", Diab. Nutr. Metab., vol. 3, 1988, pp. 227-233.
Walsh, et al., Pumping Insulin: The Art of Using an Insulin Pump. Published by MiniMed• Technologies. (1989).
Wang, Joseph, et al., "Needle-Type Dual Microsensor for the Simultaneous Monitoring of Glucose and Insulin", Analytical Chemistry, vol. 73, 2001, pp. 844-847.
Yamasaki, Yoshimitsu, et al., "Direct Measurement of Whole Blood Glucose by a Needle-Type Sensor", Clinics Chimica Acta, vol. 93, 1989, pp. 93-98.
Yokoyama, et al., "Integrated Biosensor for Glucose and Galactose", Analytica Chimica Acta, vol. 218, 1989, pp. 137-142.
(Animas Corporation, 1999). Animas . . . bringing new life to insulin therapy.
(Intensive Diabetes Management, 1995). Insulin Infusion Pump Therapy. pp. 66-78.
(Medtronic MiniMed, 2002). Medtronic MiniMed Meal Bolus Calculator and Correction Bolus Calculator. International Version.
(Medtronic MiniMed, 2002). The 508 Insulin Pump A Tradition of Excellence.

(56) References Cited

OTHER PUBLICATIONS (MiniMed Inc., 1999). Insulin Pump Comparison / Pump Therapy Will Change Your Life.
(MiniMed Inc., 1999). MiniMed 508 Flipchart Guide to Insulin Pump Therapy.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Diabetes Management.
(MiniMed Inc., 2000). Now [I] Can MiniMed Pump Therapy.
(MiniMed International, 1998). MiniMed 507C Insulin Pump For those who appreciate the difference.
(MiniMed Technologies, 1994). MiniMed 506 Insulin Pump User's Guide.
(MiniMed Technologies, 1994). MiniMedTm Dosage Calculator Initial Meal Bolus Guidelines / MiniMed TM Dosage Calculator Initial Basal Rate Guidelines Percentage Method. 4 pages.
(MiniMed, 1996). FAQ: The Practical Things . . . pp. 1-4. Retrieved on Sep. 16, 2003 from the World Wide Web: http://web.archive.org/web/19961111054546/www.minimed.comffiles/faq_pract.htm.
(MiniMed, 1996). MiniMedTm 507 Insulin Pump User's Guide.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1997). MiniMedTM 507 Insulin Pump User's Guide.
(MiniMed, 1997). Wanted: a Few Good Belt Clips! 1 page. Retrieved on Sep. 16, 2003 from the World Wide Web: http://web.archive.org/web/19970124234559/www.minimed.comffiles/mmn002.htm.
(MiniMed, 1998). MiniMed 507C Insulin Pump User's Guide.
(MiniMed, 2000). MiniMed® 508 User's Guide.
Disetronic H-TRON® plus Quick Start Manual.
Disetronic H-TRON® plus Reference Manual.
Disetronic My Choice H-TRONplus Insulin Pump Reference Manual.
Disetronic My ChoiceTM D-TRONTm Insulin Pump Reference Manual.
International Search Report dated Oct. 31, 2002; International Application No. PCT/US2002/03299; 3 pages.
Abel , et al., "Experience with an implantable glucose sensor as a prerequiste of an artificial beta cell", Biomed. Biochim. Acta 43 (1984) 5, pp. 577-584.
Bindra, Dilbir S., et al., "Design and in Vitro Studies of a Needle-Type Glucose Sensor for a Subcutaneous Monitoring", American Chemistry Society, 1991, 63, pp. 1692-1696.
Bode , et al., "Reduction in Severe Hypoglycemia with Long-Term Continuous Subcutaneous Insulin Infusion in Type I Diabetes", Diabetes Care, vol. 19, No. 4, 324-327 (1996).
Boguslavsky, Leonid , et al., "Applications of redox polymers in biosensors", Sold State Ionics 60, 1993, pp. 189-197.
Boland , Teens Pumping it Up! Insulin Pump Therapy Guide for Adolescents. 2nd Edition. (1998).
Brackenridge , et al., Counting Carbohydrates How to Zero in on Good Control. MiniMed Technologies Inc. (1995).

Brackenridge , "Carbohydrate Gram Counting A Key to Accurate Mealtime Boluses in Intensive Diabetes Therapy", Practical Diabetology, vol. 11, No. 2, pp. 22-28. (1992).
Farkas-Hirsch , et al., Continuous Subcutaneous Insulin Infusion: A Review of the Past and Its Implementation for the Future. Diabetes Spectrum From Research to Practice, vol. 7, No. 2, pp. 80-84, 136-138. (1994).
Geise, Robert J., et al., "Electropolymerized 1,3-diaminobenzene for the construction of a 1,1'-dimethylferrocene mediated glucose biosensor", Analytica Chimica Acta, 281, 1993, pp. 467-473.
Gernet , et al., "A Planar Glucose Enzyme Electrode", Sensors and Actuators, 17, 1989, pp. 537-540.
Gernet , et al., "Fabrication and Characterization of a Planar Electromechanical Cell and its Application as a Glucose Sensor", Sensors and Actuators, 18, 1989, pp. 59-70.
Gorton , et al., "Amperometric Biosensors Based on an Apparent Direct Electron Transfer Between Electrodes and Immobilized Peroxiases", Analyst, Aug. 1991, vol. 117, pp. 1235-1241.
Gorton , et al., "Amperometric Glucose Sensors Based on Immobilized Glucose-Oxidizing Enymes and Chemically Modified Electrodes", Analytica Chimica Acta, 249, 1991, pp. 43-54.
Gough , et al., "Two-Dimensional Enzyme Electrode Sensor for Glucose", Analytical Chemistry, vol. 57, No. 5, 1985, pp. 2351-2357.
Gregg, Brian A., et al., "Cross-Linked Redox Gels Containing Glucose Oxidase for Amperometric Biosensor Applications", Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone", The Journal of Physical Chemistry, vol. 95, No. 15, 1991, pp. 5970-5975.
Hashiguchi, Yasuhiro MD, et al., "Development of a Miniaturized Glucose Monitoring System by Combining a Needle-Type Glucose Sensor With Microdialysis Sampling Method", Diabetes Care, vol. 17, No. 5, May 1994, pp. 387-389.
Heller, Adam , "Electrical Wiring of Redox Enzymes", Acc. Chem. Res., vol. 23, No. 5, May 1990, pp. 128-134.
Hirsch , et al., Intensive Insulin Therapy for Treatment of Type I Diabetes. Diabetes Care, vol. 13, No. 12, pp. 1265-1283. (1990).
Jobst, Gerhard , et al., "Thin-Film Microbiosensors for Glucose-Lactate Monitoring", Analytical Chemistry, vol. 68, No. 18, Sep. 15, 1996, pp. 3173-3179.
Johnson , et al., "In vivo evaluation of an electroenzymatic glucose sensor implanted in subcutaneous tissue", Biosensors & Bioelectronics, 7, 1992, pp. 709-714.
Jonsson , et al., "An Electromechanical Sensor for Hydrogen Peroxide Based on Peroxidase Adsorbed on a Spectrographic Graphite Electrode", Electroanalysis, 1989, pp. 465-468.
Kanapieniene , et al., "Miniature Glucose Biosensor with Extended Linearity", Sensors and Actuators, B.10, 1992, pp. 37-40.
Kawamori, Ryuzo , et al., "Perfect Normalization of Excessive Glucagon Responses to Intraveneous Arginine in Human Diabetes Mellitus With the Artificial Beta-Cell", Diabetes vol. 29, Sep. 1980, pp. 762-765.
Kimura , et al., "An Immobilized Enzyme Membrane Fabrication Method", Biosensors 4, 1988, pp. 41-52.

\* cited by examiner

INTERACTIVE GUIDANCE FOR MEDICAL DEVICES

CROSS-REFERENCE TO RELATED APPLICATIONS

This application is a continuation of U.S. patent application Ser. No. 15/362,642, filed Nov. 28, 2016, which is incorporated herein by reference in its entirety.

TECHNICAL FIELD

Embodiments of the subject matter disclosed herein relate generally to medical devices and more particularly to interactive guidance for medical devices.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Control schemes have been developed that allow insulin infusion pumps to monitor and regulate a user's blood glucose level in a substantially continuous and autonomous manner. However, regulating blood glucose level is still complicated by variations in a user's individual insulin response and daily activities (e.g., exercise, carbohydrate consumption, bolus administration, and the like) in conjunction with variations associated with the devices or components used to implement continuous glucose monitoring and related controls, and potentially other factors that may contribute to variations, uncertainty, or otherwise impair accuracy or reliability. Since many of the variables influencing glucose regulation and control may often be dynamically or periodically changing, some user involvement with the infusion pump may be desirable to achieve the desired performance and outcomes.

Modern devices may incorporate or support any number of potential features as well as utilizing various user interface(s), which may be unique to a particular device. Therefore, it is desirable for device manufacturers to provide additional consumer education. Traditionally, product manuals or guides documenting the various aspects of the device were provided. For some users, printed documentation can be disfavored and neglected. At the same time, due to regulatory requirements or other concerns, medical devices may not be as equipped as other computer devices for providing consumer education features electronically. Though customer service or other manufacturer support may be available by phone or email, many users tend to find invoking such services to be time consuming and inconvenient. Accordingly, there is a need to provide consumer education in a manner that is simple, convenient, and efficient to enable maximizing device performance for optimal patient outcomes.

BRIEF SUMMARY

Disclosed herein are techniques related to interactive guidance for medical devices. The techniques may be practiced using a processor-implemented method; a system comprising one or more processors and one or more processor-readable media; and/or one or more non-transitory processor-readable media.

In some embodiments, the techniques may involve identifying, by an application executing on a computing device, a user objective with respect to a medical device communicatively coupled to the computing device. The medical device may have a graphical user interface. The techniques may further involve obtaining, by the application, state information for a current state of the graphical user interface of the medical device. The techniques may also involve generating, by the application based on the current state of the graphical user interface, a guidance user interface comprising an ordered sequence of actuations of user input elements of the medical device to achieve the identified user objective. Additionally, the techniques may involve obtaining, by the application, updated state information for an updated state of the graphical user interface of the medical device. The updated state information may be obtained responsive to an actuation of a user input element of the ordered sequence of actuations of user input elements. Furthermore, the techniques may involve dynamically updating, by the application, the guidance user interface based on the updated state information.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
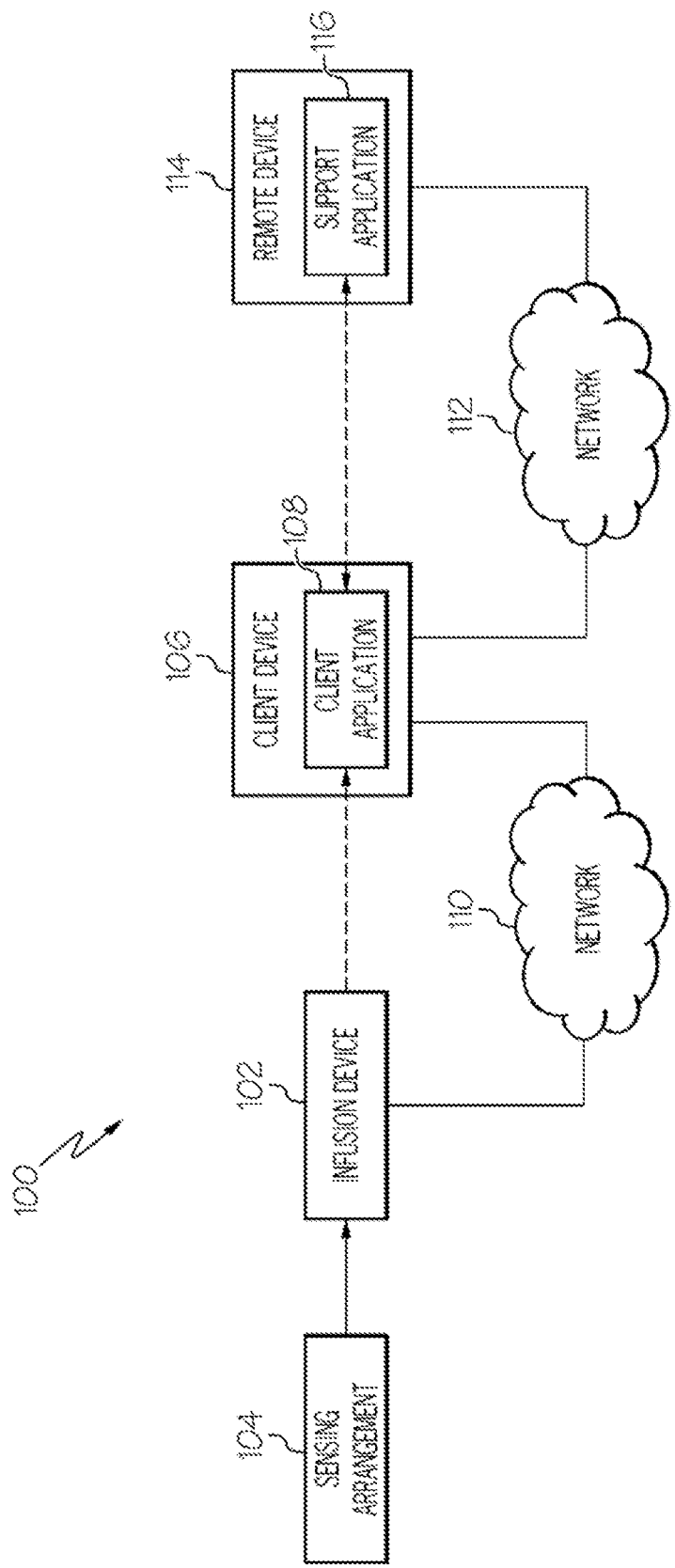
FIG. 1 depicts an exemplary embodiment of a patient guidance system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions, and the subject matter described herein is not limited to any particular type of medication or medical device being utilized.

Generally, a fluid infusion device includes a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments described herein generally relate to systems and methods of interactively providing guidance information pertaining to a medical device for review or action by a user on an auxiliary device, such as a computer, a smartphone, or the like, to help facilitate the configuration or operation of various features of a medical device. As described in greater detail below, the auxiliary device identifies or otherwise determines the user's objective associated with the medical device, such as, for example, what the user wants to accomplish using the medical device, what aspect of the medical device the user has questions about, or the like. The auxiliary device also obtains, from the medical device, status information that characterizes, describes, or otherwise corresponds to a current state of a user interface of the medical device. In this regard, the user interface status information may indicate a current graphical user interface (GUI) displayed on a display of the medical device and a current selection or position of a user input element on the display. Based on the current user interface status information and the user's objective, the guidance information indicative of the user actions for accomplishing the user's objective is determined and presented or otherwise provided on a display associated with the auxiliary device for review by the user. In this regard, the user may concurrently view the guidance information for accomplishing the objective presented on the auxiliary device while interacting with the medical device in accordance with the guidance information.

In exemplary embodiments, the auxiliary device and the medical device are paired over a communications network, so that the medical device may upload, push, or otherwise transmit updated user interface status information to the auxiliary device substantially in real-time in response to a user input or other interaction with the medical device. In response to obtaining indication of the updated state of the user interface of the medical device, the guidance information presented on the auxiliary device is dynamically updated to reflect how the user input influenced the user actions for accomplishing the user's objective from the updated user interface state. Thus, as the user navigates through various menus or GUI display screens on the medical device, the guidance information on the auxiliary device may be dynamically updated substantially concurrently, allowing the user to move back and forth across displays seamlessly.

In one or more embodiments, the auxiliary device also obtains operational settings or other device configuration information from the medical device to provide guidance information consistent with the current device setup or other user- or patient-specific configurations. For example, if the user's objective is to administer a bolus using the infusion device, the operational settings information obtained by the auxiliary device may indicate that a bolus wizard feature of the infusion device has not been setup, in which case the guidance information may provide instructions for how to configure or setup the bolus wizard. Conversely, when the operational settings information indicates the bolus wizard feature has been setup and is currently enabled, the guidance information may provide instructions for utilizing the bolus wizard. In this regard, for device features or modes that require specific user inputs, patient-specific parameters, or other actions before they are enabled or operable, the guidance information may instruct the user for configuring and enabling such features. At the same time, by virtue of obtaining the settings information, the provided guidance information does not pertain to device features or operating modes that the user has not enabled, configured, or otherwise activated. Thus, the user may be provided only with guidance information pertinent to both the current device configuration and the user's objective. As such, providing potentially non-pertinent or non-actionable information is avoided, which improves the user experience.

FIG. 1 depicts an exemplary embodiment of a patient guidance system 100. The patient guidance system 100 includes an infusion device 102 communicatively coupled to an auxiliary device 106 via a network 110. As described in greater detail below in the context of FIGS. 2-10, the auxiliary device 106 supports an application 108 that generates and provides guidance information on a display associated with the auxiliary device 108 that includes instructions or other indication of user actions for accomplishing an objective associated with the infusion device 102 based on that objective and the current user interface status for the infusion device 102 received via the network 110. In the illustrated embodiment, the infusion device 102 is also communicatively coupled to a sensing arrangement 104 to obtain measurement data indicative of a physiological condition in the body of a patient, such as sensor glucose measurement values. For example, in one or more exemplary embodiments, the infusion device 102 operates autonomously to regulate the patient's glucose level based on the sensor glucose measurement values received from the sensing arrangement 104.

The auxiliary device 106 represents an electronic device capable of communicating with the infusion device 102 via communications network 110. In exemplary embodiments, the network 110 is realized as a Bluetooth network, a ZigBee network, a wireless local area network (WLAN), or another suitable personal area network or local area network (LAN). That said, in other embodiments, the infusion device 102 and the auxiliary device 106 may communicate via a direct communications interface, such as a wire, cable, infrared, or some other short range communications medium. Depending on the embodiment, the auxiliary device 106 may be realized as any sort of electronic device capable of communicating with the infusion device 102 via network 110, such as a mobile telephone, a smartphone, a laptop or notebook computer, a tablet computer, a desktop computer, a personal digital assistant, or the like. For purposes of explanation, but without limitation, the auxiliary device 106 may alternatively be referred to herein as a client device. The client device 106 includes or is coupled to a display device, such as a monitor, screen, or another conventional electronic display, capable of graphically presenting data and/or information. The client device 106 also includes or is otherwise associated with a user input device, such as a keyboard, a mouse, a touchscreen, or the like, capable of receiving input data and/or other information from the user of the client device 106.

In one or more embodiments, a user, such as the patient, the patient's doctor or another healthcare provider, or the like, manipulates the client device 106 to execute a client application 108 that communicates with the infusion device 102 via the network 110 using a networking protocol. The client application 108 supports establishing a communications session with the infusion device 102 on the network 110 and receiving data and/or information from the infusion device 102 via the communications session. In this regard, the infusion device 102 may execute or otherwise implement a corresponding application or process that supports establishing the communications session with the client application 108. The client application 108 generally represents a software module or another feature that is generated or otherwise implemented by the client device 106 to support the processes described herein. In such embodiments, the client device 106 includes a processing system and a data storage element (or memory) capable of storing programming instructions for execution by the processing system, that, when read and executed, cause processing system to create, generate, or otherwise facilitate the client application 108 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random access memory (RAM), read only memory (ROM), flash memory, magnetic or optical mass storage, or any other suitable non-transitory short or long term data storage or other computer-readable media, and/or any suitable combination thereof.

In one or more embodiments, the infusion device 102 and the client device 106 establish an association (or pairing) with one another over the network 110 to support subsequently establishing a peer-to-peer communication session between the infusion device 102 and the client device 106 via the network 110. For example, in accordance with one embodiment, the network 110 is realized as a Bluetooth network, wherein the infusion device 102 and the client device 106 are paired with one another (e.g., by obtaining and storing network identification information for one another) by performing a discovery procedure or another suitable pairing procedure. In this regard, the pairing information obtained during the discovery procedure allows either of the infusion device 102 or the client device 106 to initiate the establishment of a secure peer-to-peer communication session via the network 110. Some examples of an infusion device pairing with a client device are described in United States Patent Application Publication Nos. 2015/0057807 and 2015/0057634, which are incorporated by reference herein in their entirety.

In one or more exemplary embodiments, the client application 108 is configured to store or otherwise maintain an address and/or other identification information for a remote device 114 on another network 112. In this regard, the second network 112 may be physically and/or logically distinct from the network 110, such as, for example, the Internet, a cellular network, a wide area network (WAN), or the like. The remote device 114 generally represents a computing device that includes or otherwise implements a support application 116 configured to receive or otherwise obtain the current user interface status information for the infusion device 102 and the current user objective from the client application 108 and present the information to another user operating the remote device 114 for analysis. For example, the remote device 114 may be utilized by customer service personnel to provide customer support in the event the patient or user of the client device 108 is having difficulty accomplishing his or her objective with respect to the infusion device 102, as described in greater detail below in the context of FIG. 2. The remote device 114 may reside at a location that is physically distinct and/or separate from the infusion device 102, such as, for example, at a facility that is owned and/or operated by or otherwise affiliated with a manufacturer of the infusion device 102.

It should be appreciated that FIG. 1 depicts a simplified representation of a patient guidance system 100 for purposes of explanation and is not intended to limit the subject matter described herein in any way. For example, in various embodiments, one or more of the devices 102, 104, 106, 114 may be absent from the patient guidance system 100. Additionally, while FIG. 1 depicts a single sensing arrangement 104, in practice, embodiments of the patient guidance system 100 may include multiple different sensing arrangements, which may be configured to sense, measure, or otherwise quantify any number of conditions or characteristics. For example, multiple instances of a glucose sensing arrangement 104 may be deployed for redundancy or other purposes (e.g., averaging or other statistical operations). In other embodiments, additional sensing arrangements 104 may be deployed to measure different physiological conditions of the patient, such as, for example, the patient's heart rate, oxygen levels, or the like.

Figure 2:
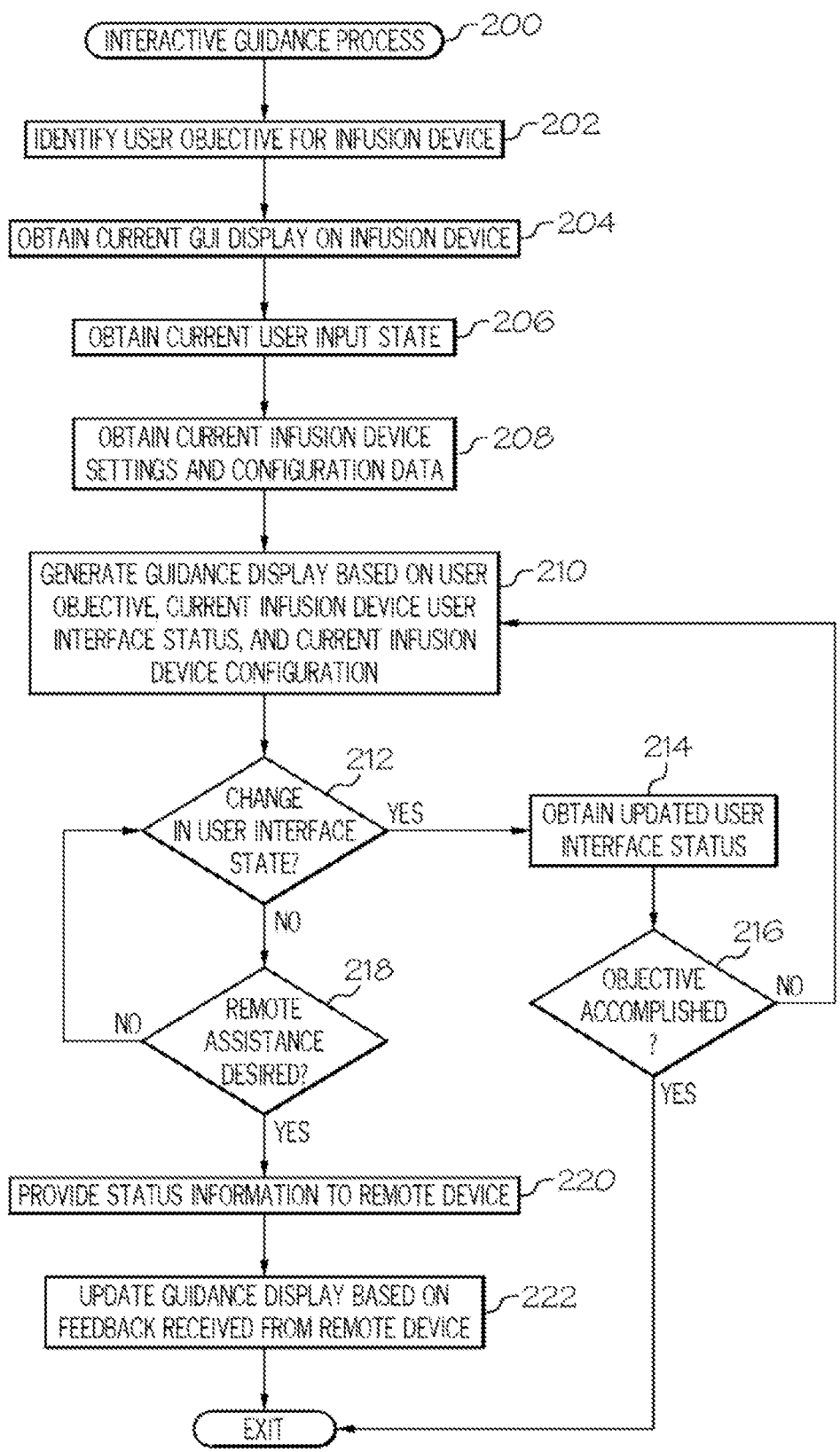
FIG. 2 is a flow diagram of an exemplary interactive guidance process suitable for use with the patient guidance system of FIG. 1 in one or more exemplary embodiments.

FIG. 2 depicts an exemplary interactive guidance process 200 suitable for implementation by a patient guidance system to provide guidance to a patient or user to facilitate desired operation of a medical device, such as infusion device 102. The various tasks performed in connection with the interactive guidance process 200 may be performed by hardware, firmware, software executed by processing circuitry, or any combination thereof. For illustrative purposes, the following description refers to elements mentioned above in connection with FIG. 1. In practice, portions of the interactive guidance process 200 may be performed by different elements of the patient guidance system 100, such as, for example, the infusion device 102, the sensing arrangement 104, the client device 106, the client application 108, the remote device 114 and/or the support application 116. It should be appreciated that the interactive guidance process 200 may include any number of additional or alternative tasks, the tasks need not be performed in the illustrated order and/or the tasks may be performed concurrently, and/or the interactive guidance process 200 may be incorporated into a more comprehensive procedure or process having additional functionality not described in detail herein. Moreover, one or more of the tasks shown and described in the context of FIG. 2 could be omitted from a practical embodiment of the interactive guidance process 200 as long as the intended overall functionality remains intact.

The interactive guidance process 200 begins by determining or otherwise identifying an objective associated with operation of the medical device (task 202). In this regard, the client application 108 identifies what the patient or user of the client device 106 is trying to accomplish or achieve using the infusion device 102 or what feature or aspect of the infusion device 102 is of interest to the patient. For example, the client application 108 may generate or otherwise provide a GUI display that allows the patient to select, input, or otherwise indicate what the patient's objective is. In one embodiment, the client application 108 generates a list of selectable GUI elements, where each of the GUI elements corresponds to a different objective, as described in greater detail below in the context of FIG. 3.

In other embodiments, the client application 108 may determine what the patient's objective is based on the current state of the infusion device 102. For example, when the patient manipulates the client device 106 to initiate or open the client application 108, the client application 108 may establish a communications session with the infusion device 102 via the network 110, obtain information characterizing the current device state from the infusion device 102 via the network 110, and then determine a likely patient objective based on the current device state. In this regard, if there is an active alert or notification presented to generated by the infusion device 102, the client application 108 may determine the patient's objective is to resolve or understand the current alert or notification. As another example, if the delivery of fluid by the infusion device 102 is suspended, the client application 108 may determine the patient's objective is to enable or resume delivery. It should be noted that are numerous different potential device statuses and corresponding objectives that may be determined based thereon, and the subject matter described herein is not limited to any particular example described herein.

In other embodiments, the client application 108 may determine what the patient's objective is based on a GUI element selected within the client application 108. For example, the client application 108 may include a selectable GUI element for activating a help feature, and thereby indicate a patient objective indicative of a desire to obtain explanatory information or other help understanding the GUI display currently presented by the infusion device 102.

The interactive guidance process 200 continues by obtaining status information indicative of the current state of the display on the medical device, the current state of the user input element(s) associated with the medical device, and the current operational settings or configuration of the medical device (tasks 204, 206, 208). In this regard, the client application 108 receives or otherwise obtains, from the infusion device 102 via the network 110, information or data that indicates, identifies, or otherwise describes the current screen, menu, or other GUI display presented on the infusion device 102. The client application 108 also receives or obtains information that indicates or identifies the state of a user input selection (or a mouse, icon, or other graphical representation thereof) on the screen, menu, or other GUI display presented on the infusion device 102. The client application 108 may also obtain information pertaining to preceding user inputs or the sequence of user input selections made prior to performing the interactive guidance process 200. Additionally, the client application 108 obtains settings or configuration data stored or otherwise maintained onboard the infusion device 102 pertaining to the various modes, features, or other patient-specific or patient-configurable operations supported by the infusion device 102. In this regard, the current device settings information may indicate the modes or features supported by the infusion device 102 that have been enabled, activated, or configured, which modes or features supported by the infusion device 102 that have been disabled or deactivated, which patient-specific control parameters, variables, or other patient settings for which values have been defined, entered or otherwise provided, and which patient-specific control parameters, variables, or other patient settings for which no values are maintained by the infusion device 102.

Based on the user's objective, the current user interface status, and the current device settings, the interactive guidance process 200 generates or otherwise provides a guidance GUI display on the auxiliary device that indicates or otherwise explains how the user can achieve the objective given the current user interface status and the current device settings (task 210). For example, the guidance GUI display on the client device 106 may provide one or more instructions or actions that the user can take from the current GUI display on the infusion device 102 given the current state of the user input(s) associated with the infusion device 102 and the current infusion device settings. In this regard, the guidance information provided by the application 108 on the client device 106 is consistent with (or context-sensitive to) both the current infusion device operational settings and the current patient-specific settings maintained by the infusion device 102, while also being context-sensitive with respect to the user interfaces of the infusion device 102 to reflect the current GUI display on the infusion device 102 and current state of user interaction with respect to that GUI display on the infusion device 102. In other words, the guidance information is not incompatible or inconsistent with current settings maintained by the infusion device 102, and is also not incompatible or inconsistent with the current user interface status of the infusion device 102.

After initially providing guidance information, the interactive guidance process 200 continues by monitoring or otherwise waiting for changes in the user interface state of the medical device, an in response to a change in the user interface state, the interactive guidance process 200 receives or otherwise obtains updated user interface status information from the medical device and dynamically updates the guidance information to reflect the change in user interface state (tasks 210, 212, 214). In this regard, as the patient or other user interacts with the user interface element(s) associated with the infusion device 102 to navigate through or change the GUI display presented on the infusion device 102, the corresponding updated status information characterizing the state or location of the user input element(s) associated with the infusion device 102 as well as the current display state of the infusion device 102 is automatically provided to the client application 108. For example, in one embodiment, a process or application on the infusion device 102 that supports the communication session with the client application 108 automatically pushes updated user interface status information to the client application 108 whenever a new user input is received or whenever the GUI display on the infusion device 102 changes. Thus, the client application 108 automatically obtains the updated user interface status information substantially in real-time and dynamically refreshes or updates the GUI display on the client device 106 to reflect the current situation on the infusion device 102, for example, by providing updated instructions or actions that the user can take to achieve the original objective (e.g., task 202) from the updated GUI display on the infusion device 102 in response to intervening user input(s) associated with the infusion device 102 after the preceding guidance GUI display was originally provided.

In exemplary embodiments, as described in greater detail below in the context of FIGS. 4-8, the loop defined by tasks 210, 212, 214 and 216 repeats to dynamically update the guidance GUI display on the client device 106 substantially in real-time as the patient or user interacts with the infusion device 102 until the original objective is accomplished. In this regard, once the application 108 determines that the updated user interface status corresponds to the user objective being accomplished (e.g., when the user has performed all the actions or instructions provided by the guidance GUI display and the display on the infusion device 102 corresponds to the intended destination GUI display at the end of the sequence of instructed user actions), the client application 108 may update the GUI display on the client device 106 to reflect the objective being achieved or to revert back to a default or initial GUI display associated with the client application 108 (e.g., a home page or other landing page).

Still referring to FIG. 2, in accordance with one or more embodiments, the interactive guidance process 200 may identify or otherwise determine when remote assistance or other supplementary feedback is desired by the user, and in response, transmits, uploads, or otherwise provides the user objective and status information to a remote device for analysis (tasks 218, 220). For example, the guidance GUI display provided by the client application 108 on the client device 106 may include a GUI element that is selectable or otherwise manipulable to initiate a customer support communications session with a customer support application 118 on a remote device 114. In this regard, the client application 108 may store or otherwise maintain an address and/or other identification information for the remote device 116 on the second network 112 to support establishing a secure communications session over the network 112 for uploading or otherwise transmitting information characterizing the current user objective, the current state of the display on the infusion device 102, the current state of the user input element(s) associated with the infusion device 102, and the current settings or configuration of the infusion device 102. In some embodiments, the client application 108 may be adapted to allow the user of the client device 106 to input or otherwise provide questions that the user would like answered or otherwise explain the user's perception of the current situation and/or what the user would like to accomplish. Additionally, in some embodiments, the client application 108 may include a GUI element (e.g., a button or the like) that enables the user of the client device 106 to initiate a telephone call, a video call, or the like with a user of the remote device 116.

The customer support application 118 on the remote device 116 is configured to generate or otherwise provide a GUI display on the remote device 116 that allows a remote user (e.g., a customer service specialist or the like) to review and analyze the current situation at the infusion device 102 and provide corresponding feedback back to the user of the client device 106 to facilitate achieving the user's objective with respect to the infusion device 102. For example, the user of the remote device 116 may input or otherwise provide a textual explanation or feedback regarding the current status at the infusion device 102 relative to the current user objective via the support application 118 and then select or otherwise manipulate a GUI element of the support application 118 to transmit the feedback back to the client application 108 via the communications session over the network 112. In this regard, the interactive guidance process 200 may update the guidance GUI display based on feedback received from the remote device (task 222). For example, the client application 108 may generate or otherwise provide the feedback received from the support application 116 on the guidance GUI display in lieu of the previously presented guidance information or on a separate GUI display (e.g., a pop-up window).

In some embodiments, the support session may be dynamically updated in a similar manner as described above in the context of the loop defined by tasks 210, 212, 214 and 216. In such embodiments, updated status information from the infusion device 102 may be automatically pushed or uploaded to the support application 118 on the remote device 116 by the client application 108 (e.g., tasks 214, 220), thereby enabling the user at the remote device 116 to monitor the state of the infusion device 102 substantially in real-time as the user interacts with the infusion device 102 and responds to the feedback from the remote device 116. As needed, the user of the support application 118 may provide updated feedback or guidance to the client application 108, which, in turn is presented on the client device 106 (e.g., tasks 220, 222).

FIGS. 3-8 depict an exemplary sequence of GUI displays that may be presented on an infusion device 302 (e.g., infusion device 102) and a paired auxiliary device 306 (e.g., client device 106) having a guidance application (e.g., client application 108) supporting the interactive guidance process 200 of FIG. 2 executing thereon. As described in greater detail below in the context of FIGS. 12-13, the infusion device 302 includes a display 326 (e.g., display 1226) and user input elements 332, 334 (e.g., user interface elements 1232, 1234) that allow a user to navigate and interact with the GUI displays presented on the display 326. The client device 306 also similarly includes a display having a guidance GUI display 308 generated by the client application 108 presented thereon.

Figure 3:
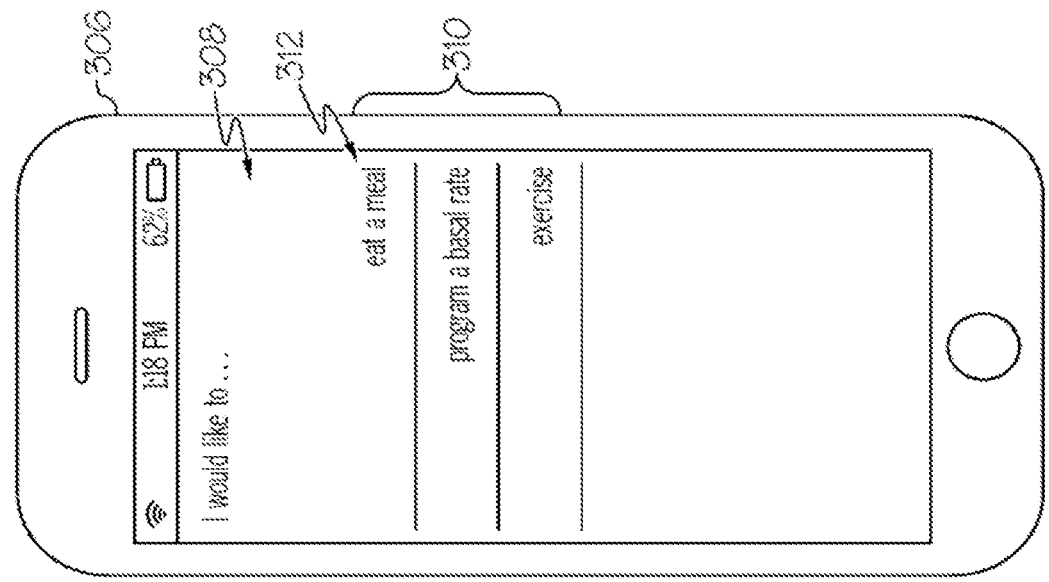
FIGS. 3-8 depict a sequence of graphical user interface displays that may be presented in conjunction with the interactive guidance process of FIG. 2 in one embodiment.
Figure 3:
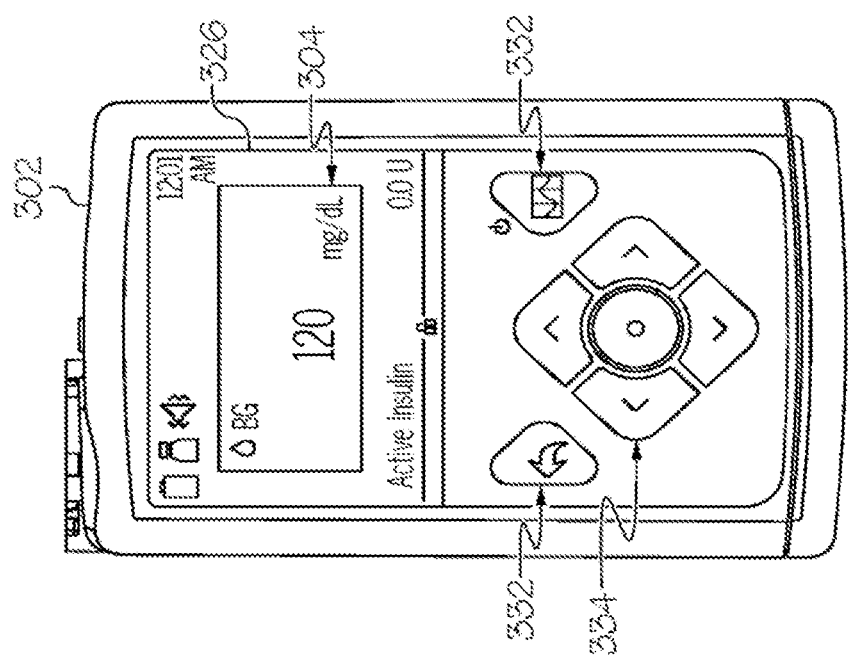

Referring to FIG. 3 with continued reference to FIGS. 1-2, FIG. 3 depicts a scenario where the infusion device 302 is presenting the main or primary GUI display 304 for the infusion device 302 (e.g., the "Home Screen"). For example, the main GUI display 304 may include standard graphical icons for the current date, time, and other physical device status information (e.g., battery level, network connectivity, fluid remaining in the reservoir, and the like) along with graphical representations of the current state of the physiological condition in the body of the user based on measurement data received from a sensor (e.g., sensing arrangement 104). The user of the client device 306 may manipulate the user input elements of the device 306 to initiate, execute, or otherwise open the client application 108, which, in turn, establishes a communications session with the infusion device 302 and obtains status information describing the current state of the display 326 (e.g., the currently displayed GUI display 304), the current state of the user input elements 332, 334 (including the location of a pointer, mouse, or other user election on or within the currently displayed GUI display 304), and the current settings stored or maintained by the infusion device 302 for the various modes or features supported by the infusion device 302 and any customizable or patient-specific parameter values. Based on the current GUI display 304 on the infusion device 302 corresponding to the home screen, the client application 108 may generate an initial GUI display 308 that enables a user to input or otherwise provide indication of his or her objective with respect to the infusion device 302. In this regard, the initial GUI display 308 may include a list 310 of potential objectives that are selectable by the user.

Figure 4:
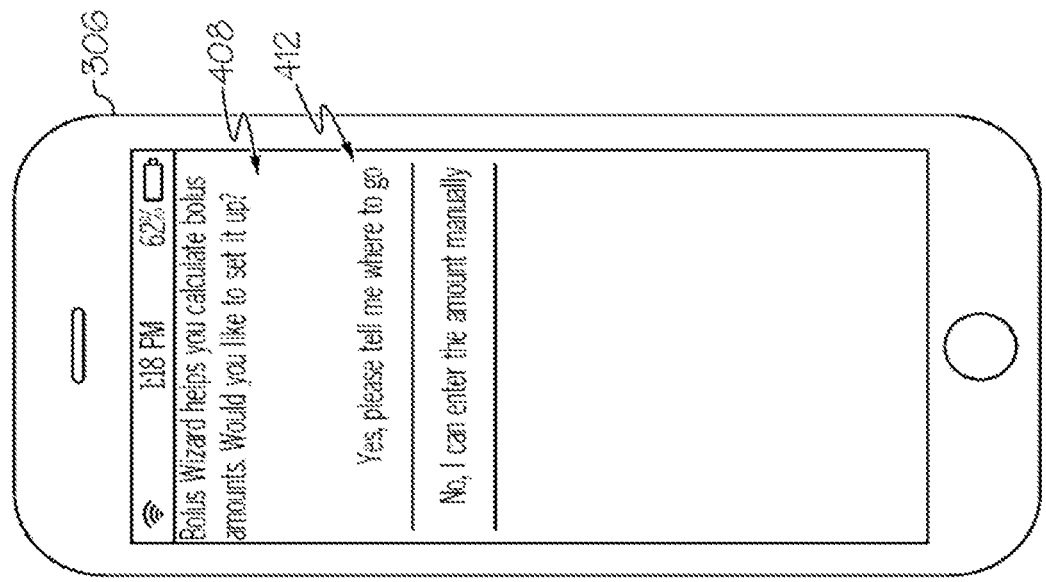
Figure 4:
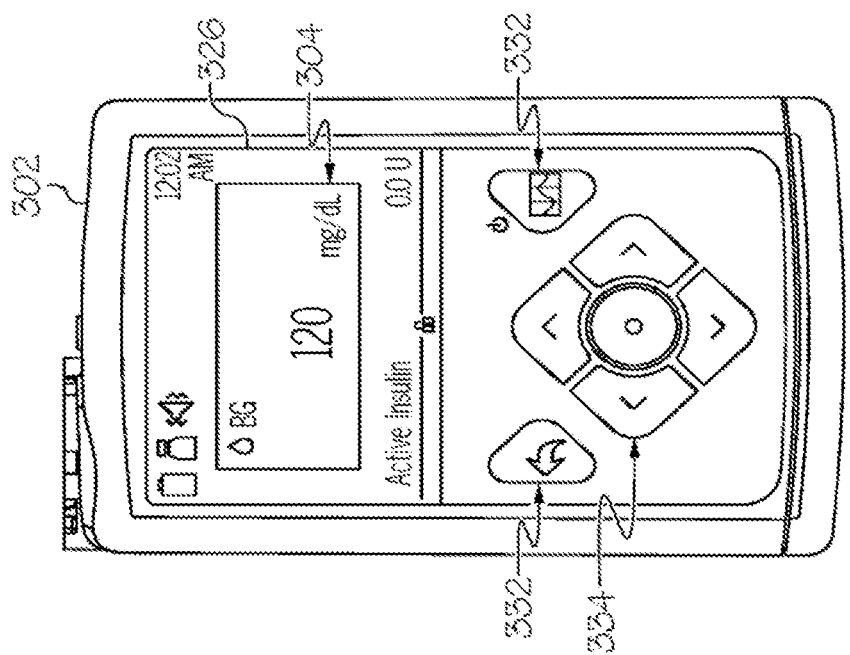

Referring now to FIG. 4, in response to the user selecting an objective 312 indicative of a desire to consume a meal (or administer a corresponding meal bolus), the client application 108 accesses the current device settings information obtained from the infusion device 302 (e.g., task 208) to verify or otherwise determine whether a bolus wizard feature has been configured or enabled by the user, and in response to determining that the current device setting information indicates the bolus wizard is not configured or enabled, the client application 108 generates a guidance GUI display 408 that enables the user to input or otherwise provide indication of whether he or she would like to configure and enable the bolus wizard or whether he or she would like to bolus manually.

Figure 5:
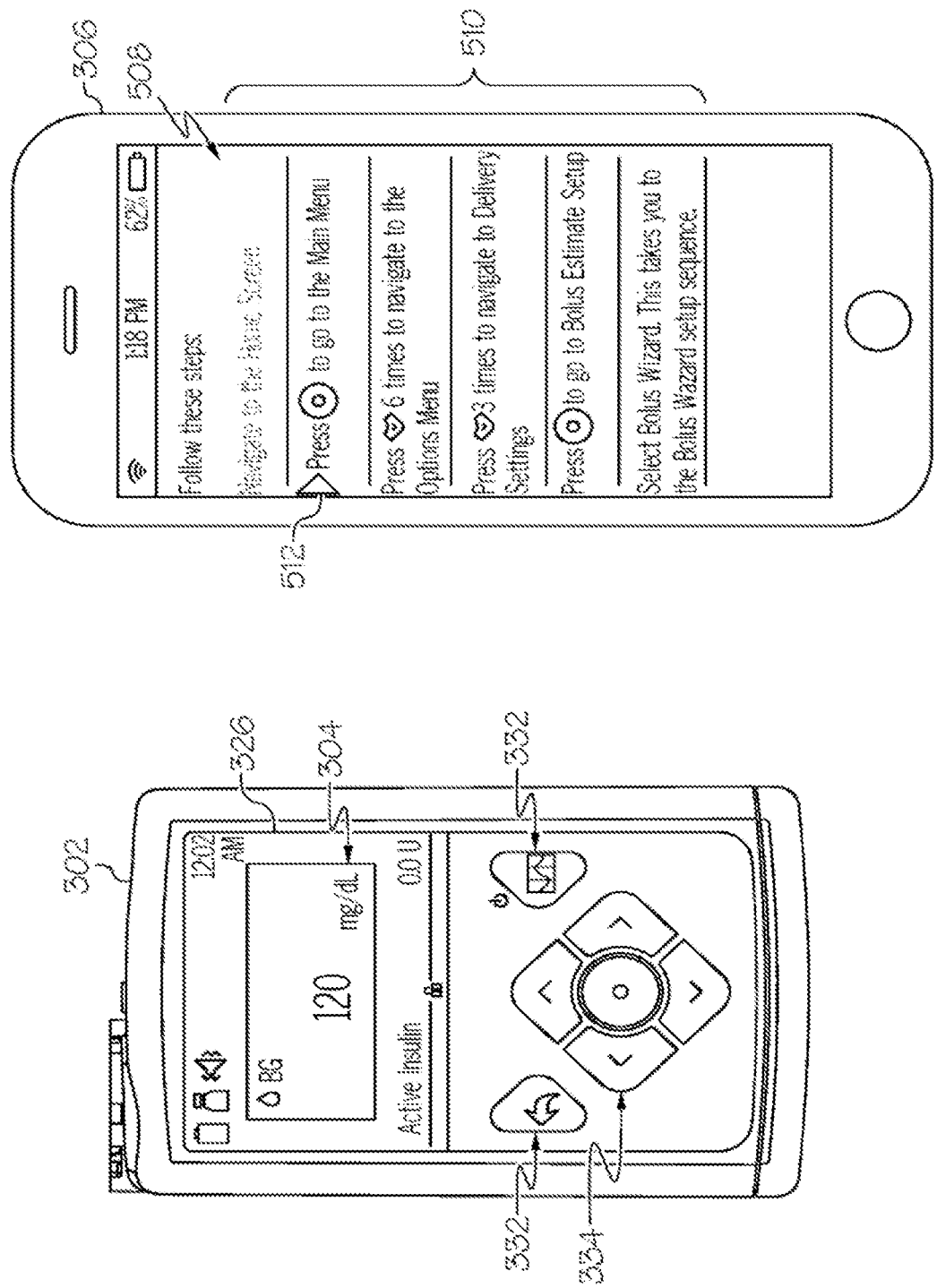

Referring now to FIG. 5, in response to selection of a GUI element 412 for configuring the bolus wizard, the client application 108 revises the user objective to enabling the bolus wizard on the infusion device 302 and then generates an updated guidance GUI display 508 including a list or sequence of actions for the user to take using the input elements 332, 334 of the infusion device 302 to achieve the objective of enabling the bolus wizard feature. In this regard, the updated guidance GUI display 508 includes a list 510 of user actions ordered sequentially for reaching the bolus wizard setup screen(s) from the "Home Screen." The guidance GUI display 508 indicates which user input elements 332, 334 on the infusion device 302 should be actuated or manipulated by the user, the ordered sequence in which those user input elements 332, 334 should be actuated, and the number of times a given user input element 332, 334 should be actuated before moving on to another user input element 332, 334 or the next action of the sequence. A graphical indicia 512 is also presented on the list 510 at the location of the entry for the step in the sequence that the user currently needs to perform. Additionally, entries that have been performed may be graphically deemphasized to reflect their performance and further indicate, to the user, where the user resides within the sequence of actions. As illustrated, the first entry in the list 510 for navigating to the "Home Screen" is graphically deemphasized to reflect the current display status of the display 326 and indicate, to the user, where the user resides within the sequence of actions.

Figure 6:
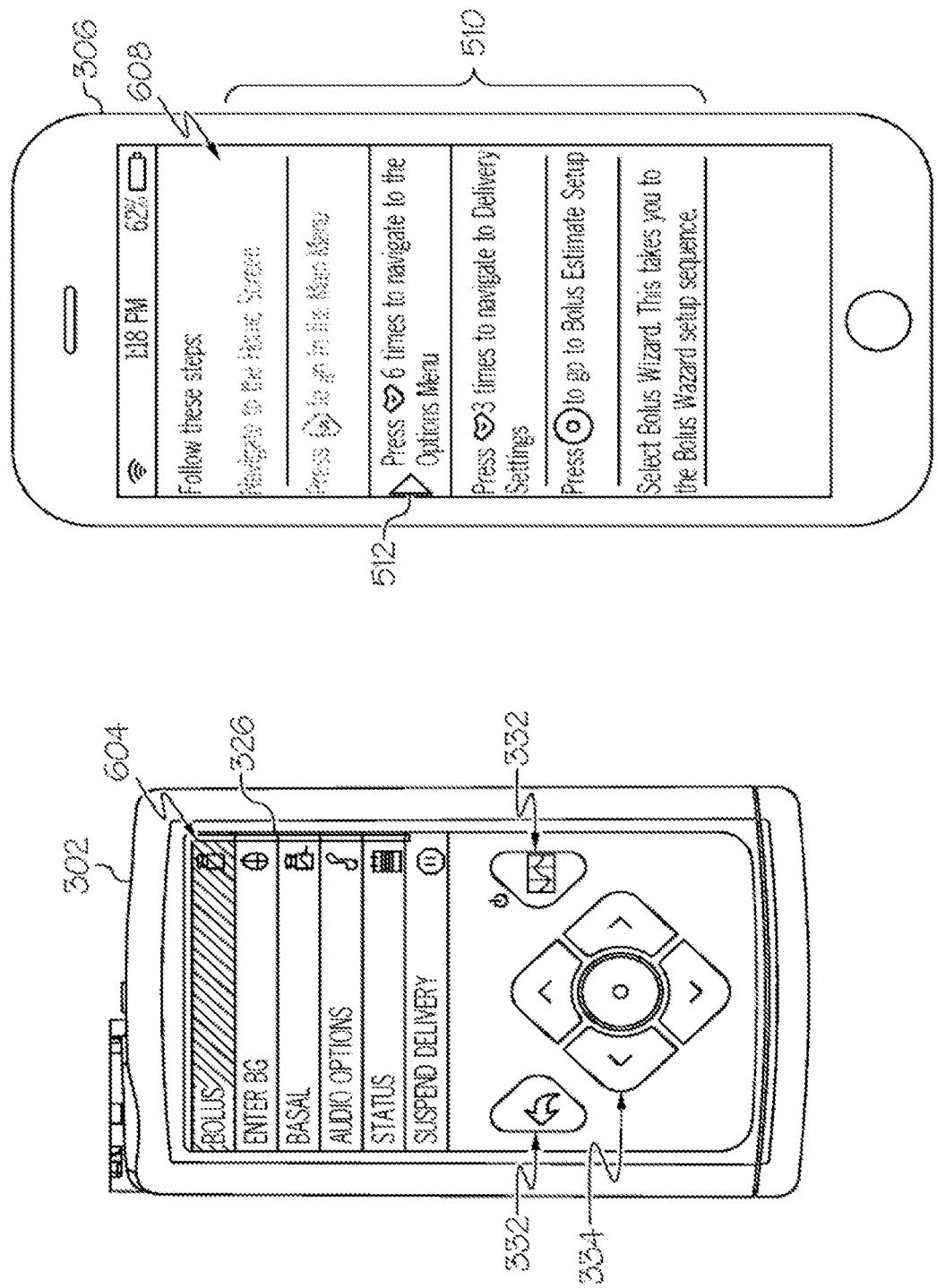
Figure 7:
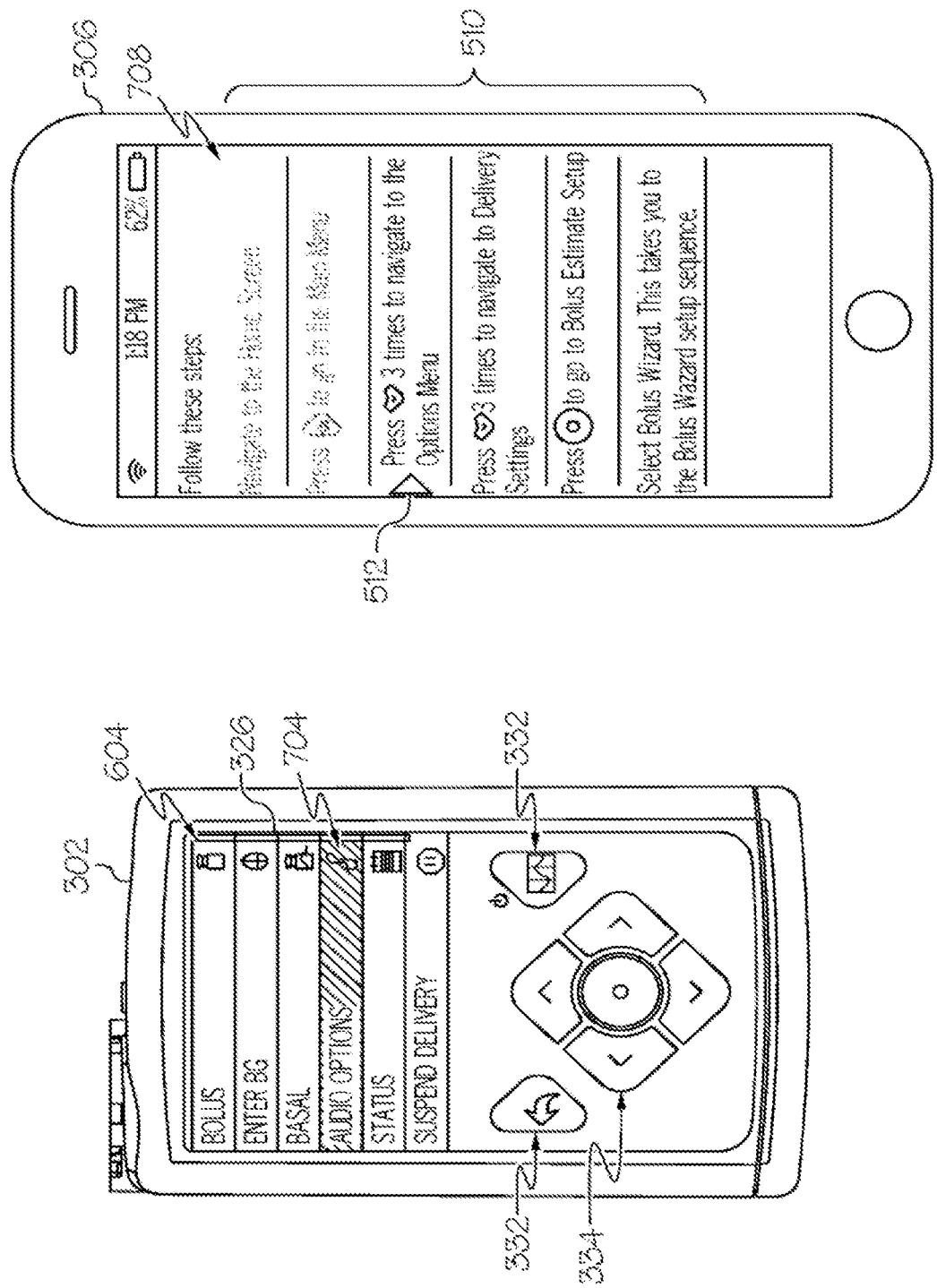
Figure 8:
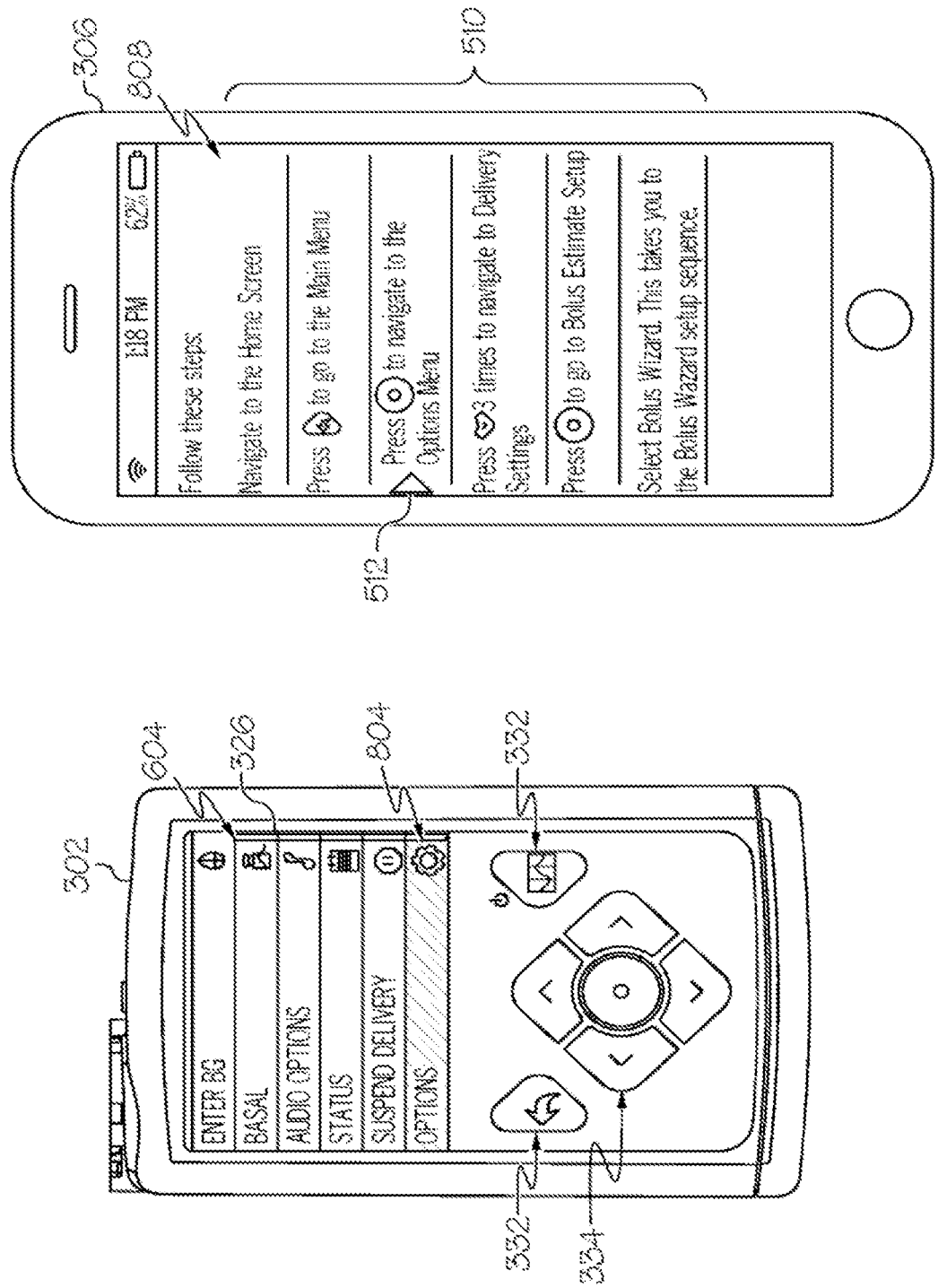

Referring now to FIGS. 6-8, in response to a user manipulating a user input element 332, 334 of the infusion device 302, updated user interface status information is automatically pushed from the infusion device 302 to the client application 108 on the client device 306 for dynamically updating the GUI display. For example, referring to FIG. 6 with reference to FIG. 5, in response to the user actuating the center button on the directional pad 334 when the Home Screen GUI display 304 is presented, the infusion device 302 updates the display 326 to present the Main Menu GUI display 604 and automatically provides updated status information to the client application 108 on the client device 306 that indicates the center button on the directional pad 334 was actuated and that the Main Menu GUI display 604 is currently presented. In response to the updated user interface status information, the client application 108 dynamically generates an updated guidance GUI display 608 that reflects the updated user interface status. For example, the second entry in the list 510 for navigating to the "Main Menu" is graphically deemphasized to reflect the current display status of the display 326 and the location of the graphical indicia 512 on the list 510 is updated indicate that the user is now on the third entry within the sequence of actions. Additionally, the entry for navigating to the "Main Menu" is updated to reflect a different user action or different user input element 332, 334 for reverting back to the preceding GUI display. Thus, the guidance GUI display 608 on the client device 306 corresponds to the state of the GUI display 604 that is concurrently being presented on the display 326 of the infusion device 302, thereby allowing the user to divert his or her attention seamlessly from the display 326 of the infusion device 302 to the guidance GUI display 608 on the client device 306 and back to the infusion device 302, while the dynamic updating of the graphical indicia 512 and other guidance information allows the user to keep track of real-time progress on the infusion device 302 when viewing the client device 306.

Referring to FIG. 7 with reference to FIG. 6, in response to the user manipulating the directional pad 334 to navigate through the Main Menu GUI display 604, the infusion device 302 automatically provides updated user interface status information to the client application 108 that indicates the current user input selection location 704 within the Main Menu GUI display 604. In response to the updated user input state 704, the client application 108 dynamically generates an updated guidance GUI display 708 that reflects a decreased number of user actions with respect to the directional pad 334 for achieving the user's objective from the current user input state 704. For example, after the user has actuated the down direction of the directional pad 334, the third entry in the list 510 for navigating to the "Options Menu" is updated (relative to guidance GUI display 608) to reflect that the user only needs to actuate the down direction of the directional pad 334 three more times instead of the original number of six to reach the "Options Menu" from the current selection location 704 of "Audio Options" within the Main Menu.

Referring to FIG. 8 with reference to FIG. 7, as the user manipulates the directional pad 334 to reach the "Options Menu" within the Main Menu GUI display 604, the infusion device 302 automatically provides updated user interface status information to the client application 108. In response to the updated user input selection location 804 corresponding to the "Options Menu," the client application 108 dynamically generates an updated guidance GUI display 808 to reflect a different user action. For example, after the user has actuated the down direction of the directional pad 334 six times, the third entry in the list 510 for navigating to the "Options Menu" is updated (relative to guidance GUI displays 508, 608, 708) to reflect that the user only needs to actuate the center button of the directional pad 334 to navigate from the Main Menu GUI display 604 to the Options Menu GUI display. Once the center button is actuated, the third entry in the list 510 for navigating to the "Options Menu" is graphically deemphasized to indicate that the user is now on the fourth entry within the sequence of actions as well as being updated to reflect a different user action or different user input element 332, 334 for reverting back to the preceding Main Menu GUI display 604 from the Options Menu GUI display in a similar manner as described above. The position of the graphical indicia 512 within the list 510 is also updated to horizontally align with the fourth entry in the list 510. It should be noted that if the user actuates the down direction of the directional pad 334 an excessive amount of times and passes the "Options Menu" within the Main Menu GUI display 604, the third entry in the list 510 for navigating to the "Options Menu" is updated (relative to guidance GUI displays 508, 608, 708) to reflect that the user only needs to actuate the up direction of the directional pad 334 to navigate to the Options Menu GUI display. In this manner, the likelihood of the user proceeding to an incorrect GUI display may be reduced.

Figure 9:
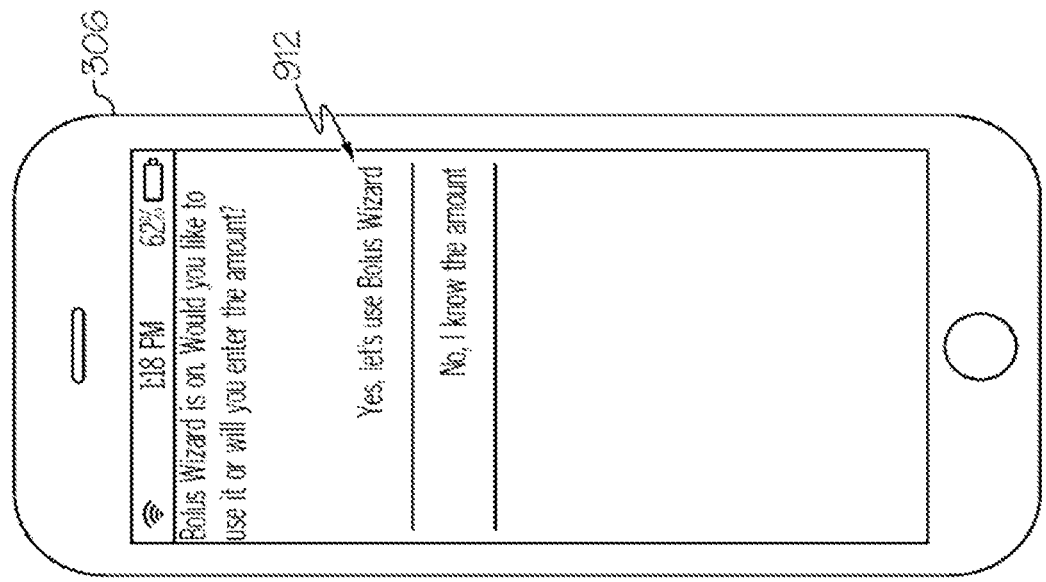
FIGS. 9-10 depict another sequence of graphical user interface displays that may be presented in conjunction with the interactive guidance process of FIG. 2 in another embodiment.
Figure 9:
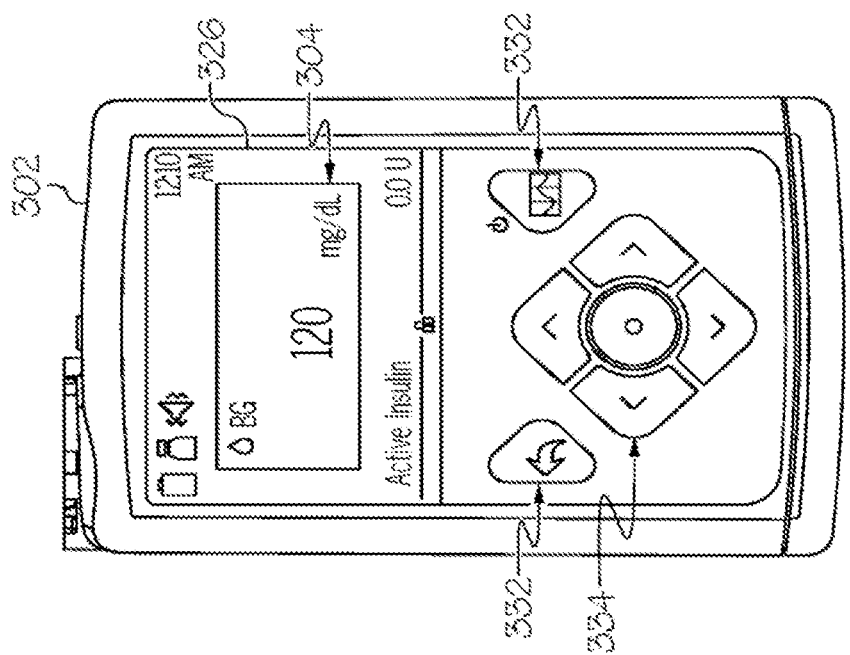
Figure 10:
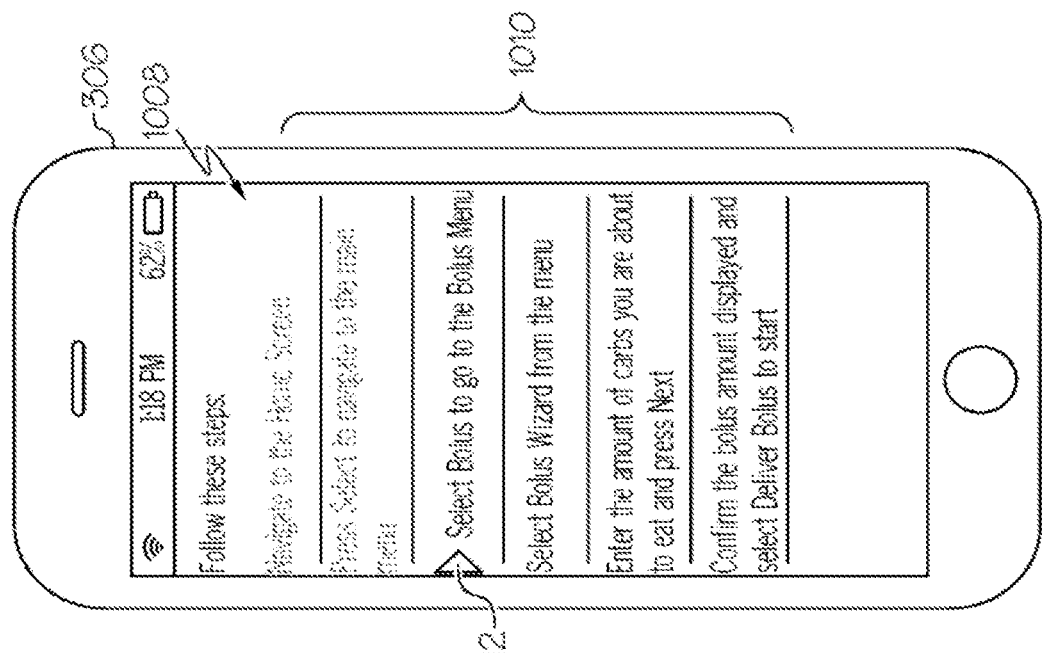
Figure 10:
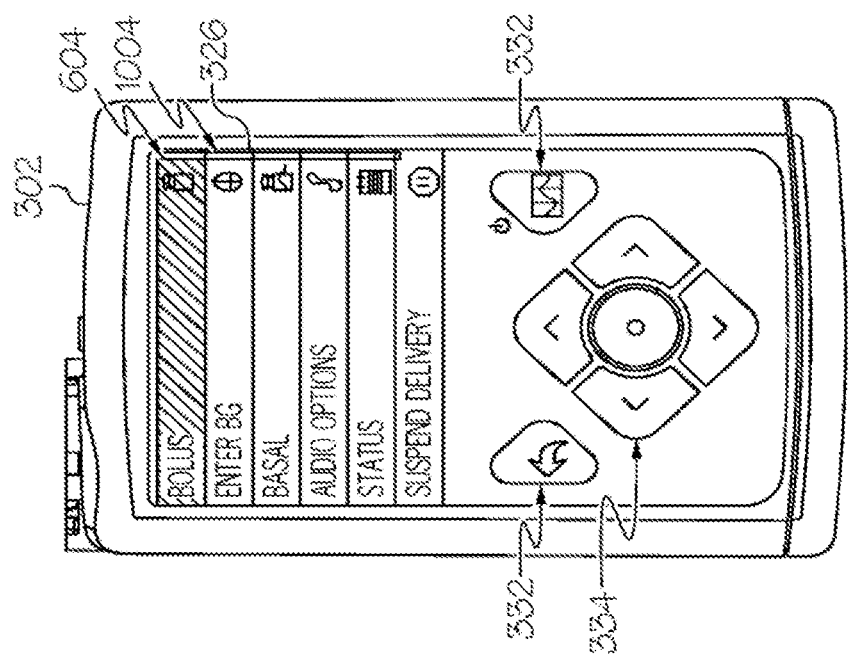

FIGS. 9-10 depict another exemplary sequence of GUI displays that may be presented on the client device 306 in concert with the infusion device 302 and the interactive guidance process 200 of FIG. 2. Referring to FIG. 9, in a similar manner as described above in the context of FIGS. 3-4, in response to the user selecting an objective 312 indicative of a desire to consume a meal (or administer a corresponding meal bolus), the client application 108 accesses the current device settings information obtained from the infusion device 302 (e.g., task 208) to verify or otherwise determine whether a bolus wizard feature has been configured or enabled by the user. In the illustrated embodiment, in response to determining that the current device settings indicate the bolus wizard is configured and enabled, the client application 108 generates a guidance GUI display 908 that enables the user to input or otherwise provide indication of whether he or she would like to utilize the bolus wizard or whether he or she would like to bolus manually.

Referring now to FIG. 10, in response to selection of a GUI element 912 for using the bolus wizard, the client application 108 generates an updated guidance GUI display 1008 to reflect the user objective of using the bolus wizard. In this regard, the updated guidance GUI display 1008 includes a list 1010 of user actions ordered sequentially for using the bolus wizard. In this regard, FIG. 10 depicts a scenario after the user has navigated from the Home Screen GUI display 304 to the Main Menu GUI display 604, with the first entry in the list 1010 for navigating to the "Home Screen" and the second entry in the list 1010 for navigating to the "Main Menu" being graphically deemphasized to reflect the current state of the display 326 in concert with the position of the graphical indicia 512 being updated based on the updated user input selection location 1004 to indicate the user is on the third entry in the list 1010. As illustrated, the list 1010 of actions presented on the guidance GUI display 1008 instructs the user how to further navigate from the Main Menu GUI display to the Bolus Menu GUI display, into the Bolus Wizard GUI display, and from there, what inputs the user should provide and the order in which the user should provide them to achieve delivery of a bolus of fluid using the bolus wizard feature.

While the above examples describe enabling or using a feature of the infusion device 102, 302, as described above, in other embodiments, the interactive guidance process 200 may be similarly employed for resolving active alerts, alarms, notifications, or other aspects of the infusion device 102, 302. For example, when the initially obtained device status information indicates an active alert, the client application 108 may automatically determine the patient's objective is to resolve or understand the current alert or notification and provide a corresponding guidance GUI display that explains the sequence of user actions that may be taken to resolve the alert. That said, the guidance GUI display may also include one or more GUI elements that allow the user to change or modify the user objective from what was automatically determined by the client application 108 based on the current display status information. In a similar manner, if delivery of fluid by the infusion device 102, 302 is suspended or some other default operating mode is inoperable or disable, the client application 108 may automatically determine the patient's objective is to enable or resume that particular operating mode and provide a corresponding guidance GUI display, which, in turn, may be modified or changed by the user if desired. In yet other embodiments, the when the patient's objective is to obtain general help or explanatory information regarding the GUI display currently presented by the infusion device 102, the client application 108 may provide a guidance GUI display that depicts a real-time representation of the GUI display that the pump is currently presenting with callouts, interactive labels, or the like describing what each GUI element on the pump GUI display means or does or other explanatory information regarding the current pump GUI display. Additionally, although not illustrated in FIGS. 3-10, some embodiments of the client application 108 may include a selectable GUI element outside of the list of user actions that allows the user of the client device 106, 306 to initiate a remote support session as described above in the context of FIG. 2.

Figure 11:
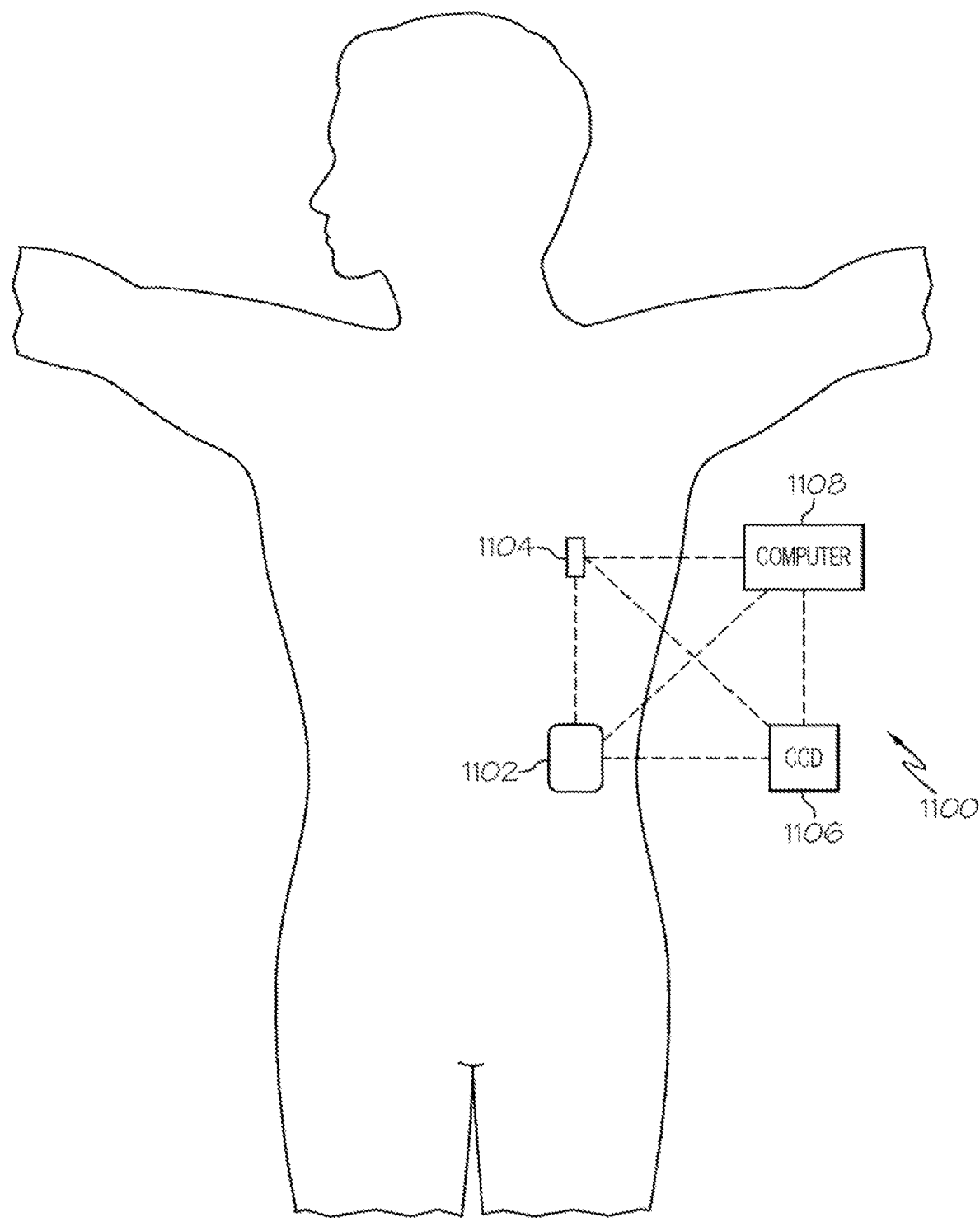
FIG. 11 depicts an exemplary embodiment of an infusion system.

FIG. 11 depicts one exemplary embodiment of an infusion system 1100 suitable for use with the patient guidance system 100 of FIG. 1 in conjunction with the interactive guidance process 200 of FIGS. 2-10. The infusion system 1100 includes, without limitation, a fluid infusion device (or infusion pump) 1102 (e.g., infusion device 102, 302), a sensing arrangement 1104 (e.g., sensing arrangement 104), a command control device (CCD) 1106, and a computer 1108, which could be realized as any one of the computing devices 106, 114, 306 described above. For example, in one embodiment, the CCD 1106 is realized as a client device 106, 306 and the computer 1108 is realized as remote device 114. The components of an infusion system 1100 may be realized using different platforms, designs, and configurations, and the embodiment shown in FIG. 11 is not exhaustive or limiting. In practice, the infusion device 1102 and the sensing arrangement 1104 are secured at desired locations on the body of a user (or patient), as illustrated in FIG. 11. In this regard, the locations at which the infusion device 1102 and the sensing arrangement 1104 are secured to the body of the user in FIG. 11 are provided only as a representative, non-limiting, example. The elements of the infusion system 1100 may be similar to those described in U.S. Pat. No. 8,674,288, the subject matter of which is hereby incorporated by reference in its entirety.

In the illustrated embodiment of FIG. 11, the infusion device 1102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 1104 generally represents the components of the infusion system 1100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 1104 may include electronics and enzymes reactive to a biological or physiological condition of the user, such as a blood glucose level, or the like, and provide data indicative of the blood glucose level to the infusion device 1102, the CCD 1106 and/or the computer 1108. For example, the infusion device 1102, the CCD 1106 and/or the computer 1108 may include a display for presenting information or data to the user based on the sensor data received from the sensing arrangement 1104, such as, for example, a current glucose level of the user, a graph or chart of the user's glucose level versus time, device status indicators, alert messages, or the like. In other embodiments, the infusion device 1102, the CCD 1106 and/or the computer 1108 may include electronics and software that are configured to analyze sensor data and operate the infusion device 1102 to deliver fluid to the body of the user based on the sensor data and/or preprogrammed delivery routines. Thus, in exemplary embodiments, one or more of the infusion device 1102, the sensing arrangement 1104, the CCD 1106, and/or the computer 1108 includes a transmitter, a receiver, and/or other transceiver electronics that allow for communication with other components of the infusion system 1100, so that the sensing arrangement 1104 may transmit sensor data or monitor data to one or more of the infusion device 1102, the CCD 1106 and/or the computer 1108.

Still referring to FIG. 11, in various embodiments, the sensing arrangement 1104 may be secured to the body of the user or embedded in the body of the user at a location that is remote from the location at which the infusion device 1102 is secured to the body of the user. In various other embodiments, the sensing arrangement 1104 may be incorporated within the infusion device 1102. In other embodiments, the sensing arrangement 1104 may be separate and apart from the infusion device 1102, and may be, for example, part of the CCD 1106. In such embodiments, the sensing arrangement 1104 may be configured to receive a biological sample, analyte, or the like, to measure a condition of the user.

In various embodiments, the CCD 1106 and/or the computer 1108 may include electronics and other components configured to perform processing, delivery routine storage, and to control the infusion device 1102 in a manner that is influenced by sensor data measured by and/or received from the sensing arrangement 1104. By including control functions in the CCD 1106 and/or the computer 1108, the infusion device 1102 may be made with more simplified electronics. However, in other embodiments, the infusion device 1102 may include all control functions, and may operate without the CCD 1106 and/or the computer 1108. In various embodiments, the CCD 1106 may be a portable electronic device. In addition, in various embodiments, the infusion device 1102 and/or the sensing arrangement 1104 may be configured to transmit data to the CCD 1106 and/or the computer 1108 for display or processing of the data by the CCD 1106 and/or the computer 1108.

In some embodiments, the CCD 1106 and/or the computer 1108 may provide information to the user that facilitates the user's subsequent use of the infusion device 1102. For example, the CCD 1106 may provide information to the user to allow the user to determine the rate or dose of medication to be administered into the user's body. In other embodiments, the CCD 1106 may provide information to the infusion device 1102 to autonomously control the rate or dose of medication administered into the body of the user. In some embodiments, the sensing arrangement 1104 may be integrated into the CCD 1106. Such embodiments may allow the user to monitor a condition by providing, for example, a sample of his or her blood to the sensing arrangement 1104 to assess his or her condition. In some embodiments, the sensing arrangement 1104 and the CCD 1106 may be used for determining glucose levels in the blood and/or body fluids of the user without the use of, or necessity of, a wire or cable connection between the infusion device 1102 and the sensing arrangement 1104 and/or the CCD 1106.

In one or more exemplary embodiments, the sensing arrangement 1104 and/or the infusion device 1102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 1104 is configured to sense or measure a condition of the user, such as, blood glucose level or the like. The infusion device 1102 is configured to deliver fluid in response to the condition sensed by the sensing arrangement 1104. In turn, the sensing arrangement 1104 continues to sense or otherwise quantify a current condition of the user, thereby allowing the infusion device 1102 to deliver fluid continuously in response to the condition currently (or most recently) sensed by the sensing arrangement 1104 indefinitely. In some embodiments, the sensing arrangement 1104 and/or the infusion device 1102 may be configured to utilize the closed-loop system only for a portion of the day, for example only when the user is asleep or awake.

Figure 12:
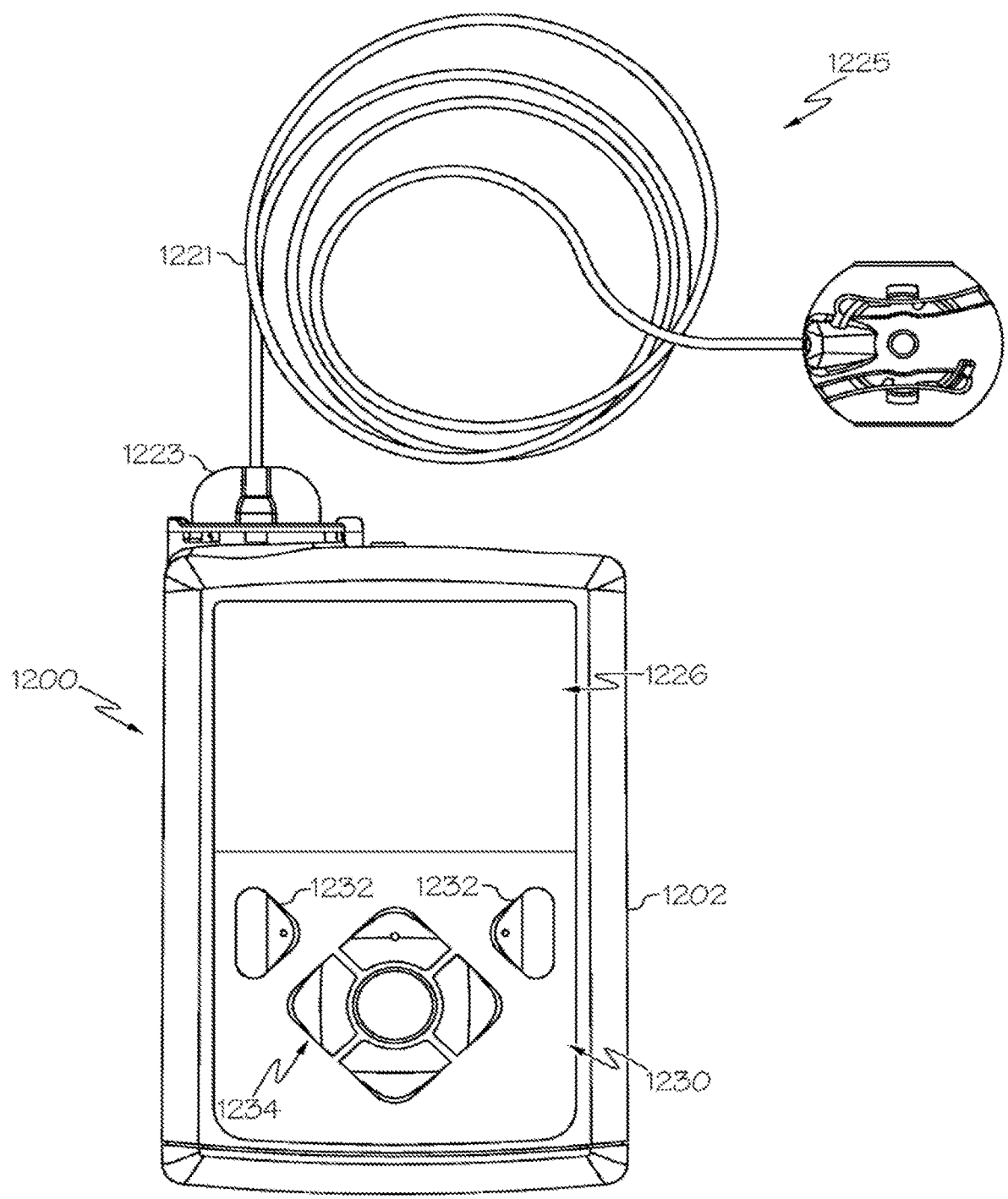
FIG. 12 depicts a plan view of an exemplary embodiment of a fluid infusion device suitable for use in the infusion system of FIG. 11.
Figure 13:
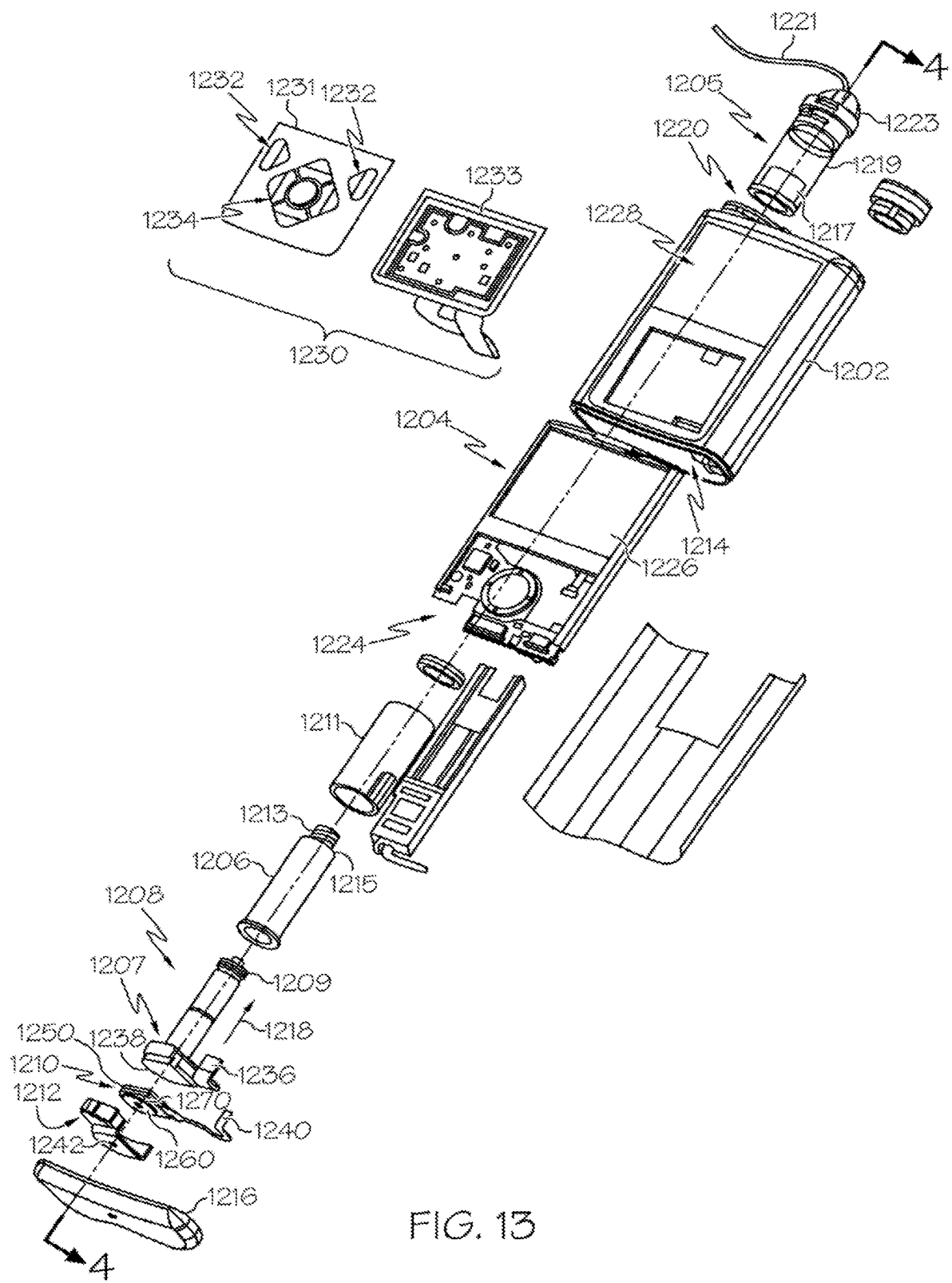
FIG. 13 is an exploded perspective view of the fluid infusion device of FIG. 12.
Figure 14:
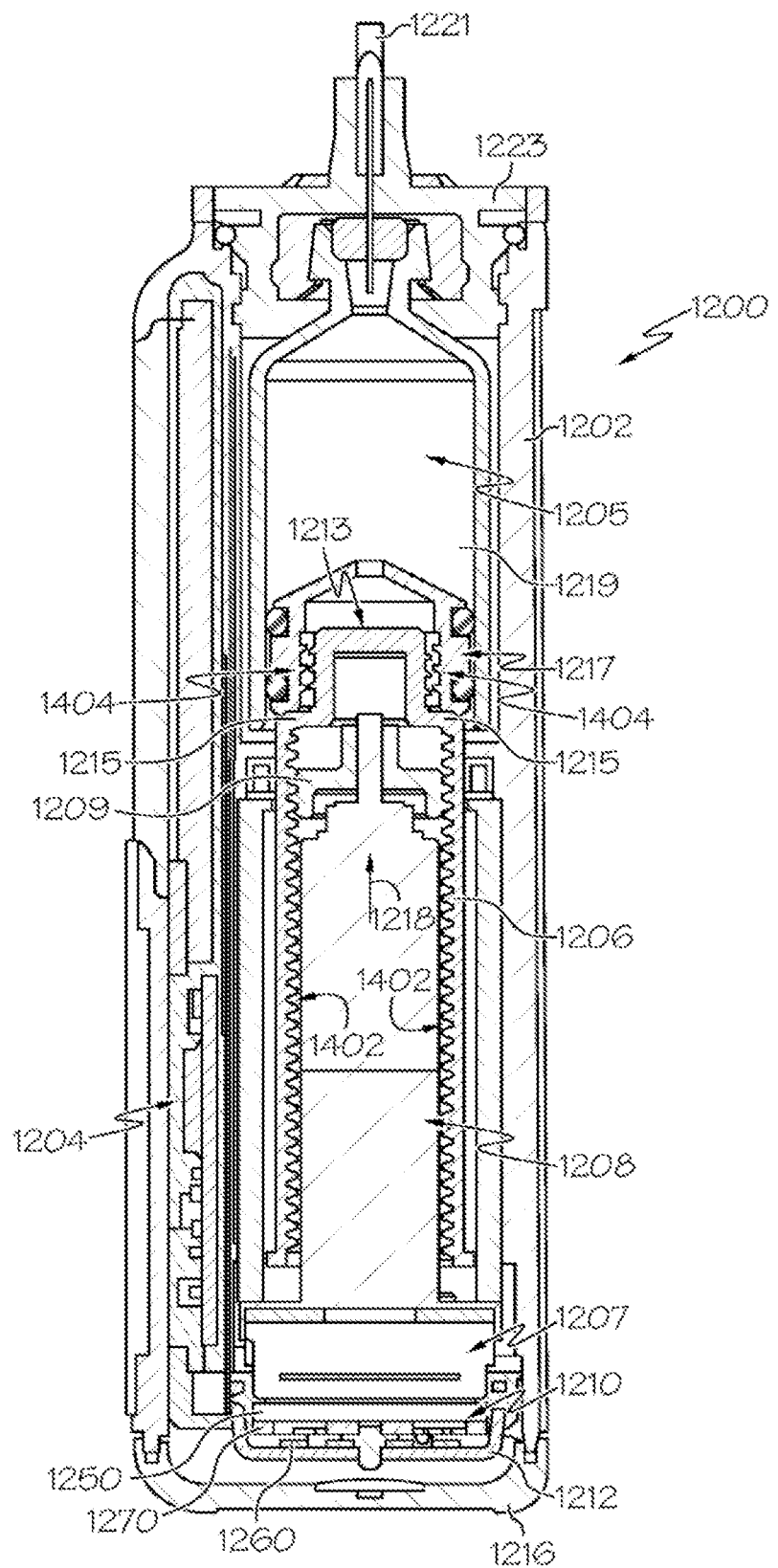
FIG. 14 is a cross-sectional view of the fluid infusion device of FIGS. 12-13 as viewed along line 14-14 in FIG. 13 when assembled with a reservoir inserted in the infusion device.

FIGS. 12-14 depict one exemplary embodiment of a fluid infusion device 1200 (or alternatively, infusion pump) suitable for use as an infusion device 102, 302, 1102 described above in the context of FIGS. 1-11. The fluid infusion device 1200 is a portable medical device designed to be carried or worn by a patient (or user), and the fluid infusion device 1200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 12-14 depict some aspects of the infusion device 1200 in a simplified manner; in practice, the infusion device 1200 could include additional elements, features, or components that are not shown or described in detail herein.

As best illustrated in FIGS. 12-13, the illustrated embodiment of the fluid infusion device 1200 includes a housing 1202 adapted to receive a fluid-containing reservoir 1205. An opening 1220 in the housing 1202 accommodates a fitting 1223 (or cap) for the reservoir 1205, with the fitting 1223 being configured to mate or otherwise interface with tubing 1221 of an infusion set 1225 that provides a fluid path to/from the body of the user. In this manner, fluid communication from the interior of the reservoir 1205 to the user is established via the tubing 1221. The illustrated fluid infusion device 1200 includes a human-machine interface (HMI) 1230 (or user interface) that includes elements 1232, 1234 that can be manipulated by the user to administer a bolus of fluid (e.g., insulin), to change therapy settings, to change user preferences, to select display features, and the like. The infusion device also includes a display element 1226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 1202 is formed from a substantially rigid material having a hollow interior 1014 adapted to allow an electronics assembly 1204, a sliding member (or slide) 1206, a drive system 1208, a sensor assembly 1210, and a drive system capping member 1212 to be disposed therein in addition to the reservoir 1205, with the contents of the housing 1202 being enclosed by a housing capping member 1216. The opening 1220, the slide 1206, and the drive system 1208 are coaxially aligned in an axial direction (indicated by arrow 1218), whereby the drive system 1208 facilitates linear displacement of the slide 1206 in the axial direction 1218 to dispense fluid from the reservoir 1205 (after the reservoir 1205 has been inserted into opening 1220), with the sensor assembly 1210 being configured to measure axial forces (e.g., forces aligned with the axial direction 1218) exerted on the sensor assembly 1210 responsive to operating the drive system 1208 to displace the slide 1206. In various embodiments, the sensor assembly 1210 may be utilized to detect one or more of the following: an occlusion in a fluid path that slows, prevents, or otherwise degrades fluid delivery from the reservoir 1205 to a user's body; when the reservoir 1205 is empty; when the slide 1206 is properly seated with the reservoir 1205; when a fluid dose has been delivered; when the infusion pump 1200 is subjected to shock or vibration; when the infusion pump 1200 requires maintenance.

Depending on the embodiment, the fluid-containing reservoir 1205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 13-14, the reservoir 1205 typically includes a reservoir barrel 1219 that contains the fluid and is concentrically and/or coaxially aligned with the slide 1206 (e.g., in the axial direction 1218) when the reservoir 1205 is inserted into the infusion pump 1200. The end of the reservoir 1205 proximate the opening 1220 may include or otherwise mate with the fitting 1223, which secures the reservoir 1205 in the housing 1202 and prevents displacement of the reservoir 1205 in the axial direction 1218 with respect to the housing 1202 after the reservoir 1205 is inserted into the housing 1202. As described above, the fitting 1223 extends from (or through) the opening 1220 of the housing 1202 and mates with tubing 1221 to establish fluid communication from the interior of the reservoir 1205 (e.g., reservoir barrel 1219) to the user via the tubing 1221 and infusion set 1225. The opposing end of the reservoir 1205 proximate the slide 1206 includes a plunger 1217 (or stopper) positioned to push fluid from inside the barrel 1219 of the reservoir 1205 along a fluid path through tubing 1221 to a user. The slide 1206 is configured to mechanically couple or otherwise engage with the plunger 1217, thereby becoming seated with the plunger 1217 and/or reservoir 1205. Fluid is forced from the reservoir 1205 via tubing 1221 as the drive system 1208 is operated to displace the slide 1206 in the axial direction 1218 toward the opening 1220 in the housing 1202.

In the illustrated embodiment of FIGS. 13-14, the drive system 1208 includes a motor assembly 1207 and a drive screw 1209. The motor assembly 1207 includes a motor that is coupled to drive train components of the drive system 1208 that are configured to convert rotational motor motion to a translational displacement of the slide 1206 in the axial direction 1218, and thereby engaging and displacing the plunger 1217 of the reservoir 1205 in the axial direction 1218. In some embodiments, the motor assembly 1207 may also be powered to translate the slide 1206 in the opposing direction (e.g., the direction opposite direction 1218) to retract and/or detach from the reservoir 1205 to allow the reservoir 1205 to be replaced. In exemplary embodiments, the motor assembly 1207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 1205.

As best shown in FIG. 14, the drive screw 1209 mates with threads 1402 internal to the slide 1206. When the motor assembly 1207 is powered and operated, the drive screw 1209 rotates, and the slide 1206 is forced to translate in the axial direction 1218. In an exemplary embodiment, the infusion pump 1200 includes a sleeve 1211 to prevent the slide 1206 from rotating when the drive screw 1209 of the drive system 1208 rotates. Thus, rotation of the drive screw 1209 causes the slide 1206 to extend or retract relative to the drive motor assembly 1207. When the fluid infusion device is assembled and operational, the slide 1206 contacts the plunger 1217 to engage the reservoir 1205 and control delivery of fluid from the infusion pump 1200. In an exemplary embodiment, the shoulder portion 1215 of the slide 1206 contacts or otherwise engages the plunger 1217 to displace the plunger 1217 in the axial direction 1218. In alternative embodiments, the slide 1206 may include a threaded tip 1213 capable of being detachably engaged with internal threads 1404 on the plunger 1217 of the reservoir

1205, as described in detail in U.S. Pat. Nos. 6,248,093 and 6,485,465, which are incorporated by reference herein.

As illustrated in FIG. 13, the electronics assembly 1204 includes control electronics 1224 coupled to the display element 1226, with the housing 1202 including a transparent window portion 1228 that is aligned with the display element 1226 to allow the display 1226 to be viewed by the user when the electronics assembly 1204 is disposed within the interior 1014 of the housing 1202. The control electronics 1224 generally represent the hardware, firmware, processing logic and/or software (or combinations thereof) configured to control operation of the motor assembly 1207 and/or drive system 1208. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 1224 includes one or more programmable controllers that may be programmed to control operation of the infusion pump 1200.

The motor assembly 1207 includes one or more electrical leads 1236 adapted to be electrically coupled to the electronics assembly 1204 to establish communication between the control electronics 1224 and the motor assembly 1207. In response to command signals from the control electronics 1224 that operate a motor driver (e.g., a power converter) to regulate the amount of power supplied to the motor from a power supply, the motor actuates the drive train components of the drive system 1208 to displace the slide 1206 in the axial direction 1218 to force fluid from the reservoir 1205 along a fluid path (including tubing 1221 and an infusion set), thereby administering doses of the fluid contained in the reservoir 1205 into the user's body. Preferably, the power supply is realized one or more batteries contained within the housing 1202. Alternatively, the power supply may be a solar panel, capacitor, AC or DC power supplied through a power cord, or the like. In some embodiments, the control electronics 1224 may operate the motor of the motor assembly 1207 and/or drive system 1208 in a stepwise manner, typically on an intermittent basis; to administer discrete precise doses of the fluid to the user according to programmed delivery profiles.

Referring to FIGS. 12-14, as described above, the user interface 1230 includes HMI elements, such as buttons 1232 and a directional pad 1234, that are formed on a graphic keypad overlay 1231 that overlies a keypad assembly 1233, which includes features corresponding to the buttons 1232, directional pad 1234 or other user interface items indicated by the graphic keypad overlay 1231. When assembled, the keypad assembly 1233 is coupled to the control electronics 1224, thereby allowing the HMI elements 1232, 1234 to be manipulated by the user to interact with the control electronics 1224 and control operation of the infusion pump 1200, for example, to administer a bolus of insulin, to change therapy settings, to change user preferences, to select display features, to set or disable alarms and reminders, and the like. In this regard, the control electronics 1224 maintains and/or provides information to the display 1226 regarding program parameters, delivery profiles, pump operation, alarms, warnings, statuses, or the like, which may be adjusted using the HMI elements 1232, 1234. In various embodiments, the HMI elements 1232, 1234 may be realized as physical objects (e.g., buttons, knobs, joysticks, and the like) or virtual objects (e.g., using touch-sensing and/or proximity-sensing technologies). For example, in some embodiments, the display 1226 may be realized as a touch screen or touch-sensitive display, and in such embodiments, the features and/or functionality of the HMI elements 1232, 1234 may be integrated into the display 1226 and the HMI 1230 may not be present. In some embodiments, the electronics assembly 1204 may also include alert generating elements coupled to the control electronics 1224 and suitably configured to generate one or more types of feedback, such as, without limitation: audible feedback; visual feedback; haptic (physical) feedback; or the like.

Referring to FIGS. 13-14, in accordance with one or more embodiments, the sensor assembly 1210 includes a back plate structure 1250 and a loading element 1260. The loading element 1260 is disposed between the capping member 1212 and a beam structure 1270 that includes one or more beams having sensing elements disposed thereon that are influenced by compressive force applied to the sensor assembly 1210 that deflects the one or more beams, as described in greater detail in U.S. Pat. No. 8,474,332, which is incorporated by reference herein. In exemplary embodiments, the back plate structure 1250 is affixed, adhered, mounted, or otherwise mechanically coupled to the bottom surface 1238 of the drive system 1208 such that the back plate structure 1250 resides between the bottom surface 1238 of the drive system 1208 and the housing cap 1216. The drive system capping member 1212 is contoured to accommodate and conform to the bottom of the sensor assembly 1210 and the drive system 1208. The drive system capping member 1212 may be affixed to the interior of the housing 1202 to prevent displacement of the sensor assembly 1210 in the direction opposite the direction of force provided by the drive system 1208 (e.g., the direction opposite direction 1218). Thus, the sensor assembly 1210 is positioned between the motor assembly 1207 and secured by the capping member 1212, which prevents displacement of the sensor assembly 1210 in a downward direction opposite the direction of arrow 1218, such that the sensor assembly 1210 is subjected to a reactionary compressive force when the drive system 1208 and/or motor assembly 1207 is operated to displace the slide 1206 in the axial direction 1218 in opposition to the fluid pressure in the reservoir 1205. Under normal operating conditions, the compressive force applied to the sensor assembly 1210 is correlated with the fluid pressure in the reservoir 1205. As shown, electrical leads 1240 are adapted to electrically couple the sensing elements of the sensor assembly 1210 to the electronics assembly 1204 to establish communication to the control electronics 1224, wherein the control electronics 1224 are configured to measure, receive, or otherwise obtain electrical signals from the sensing elements of the sensor assembly 1210 that are indicative of the force applied by the drive system 1208 in the axial direction 1218.

Figure 15:
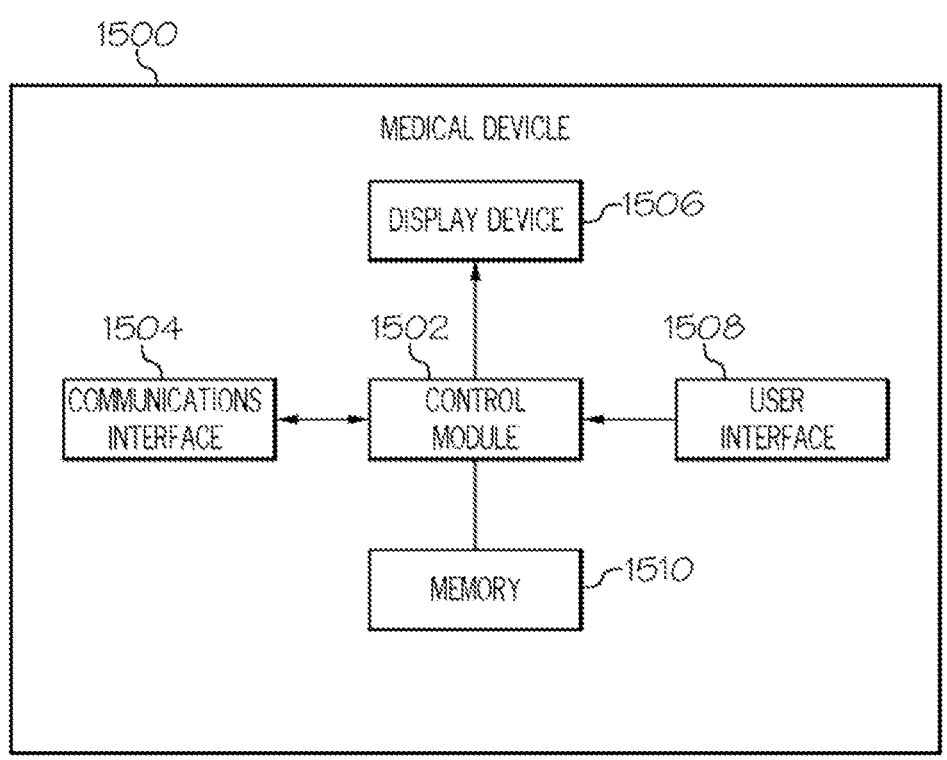
FIG. 15 is a block diagram of an exemplary medical device suitable for use in conjunction with the interactive guidance process of FIG. 2 in accordance with one or more exemplary embodiments.

FIG. 15 depicts an exemplary embodiment of a medical device 1500 suitable for use as the infusion device 102, 302, 1102, 1200 in conjunction with the interactive guidance process 200 of FIGS. 2-10. The illustrated medical device 1500 includes, without limitation, a control module 1502, a communications interface 1504, a display device 1506, a user interface 1508, and a data storage element (or memory) 1510. The control module 1502 is coupled to the communications interface 1504, the memory 1510, the display device 1506, and the memory 1006, and the control module 1502 is suitably configured to support the operations, tasks, and/or processes described herein. It should be understood that FIG. 15 is a simplified representation of a medical device 1500 for purposes of explanation and is not intended to limit the subject matter described herein in any way.

The communications interface 1504 generally represents the hardware, circuitry, logic, firmware and/or other components of the medical device 1500 that are coupled to the control module 1502 and configured to support communications sessions between the medical device 1500 and an auxiliary device (e.g., devices 106, 306, 1106) via a network (e.g., network 110). In this regard, the communications interface 1504 may include or otherwise be coupled to one or more transceiver modules capable of supporting wireless communications. In other embodiments, the communications interface 1504 may be configured to support wired communications to/from the auxiliary device.

The display device 1506 may be realized as any sort of electronic display capable of graphically displaying information or other data associated with operation of the medical device 1500 under control of the control module 1502. The user interface 1508 generally includes one or more user input devices configured to allow a patient or other user to interact with the medical device 1500 and the GUI displays presented on the display device 1506. Depending on the embodiment, the user interface 1508 may include or be realized as one or more of the following user input devices: a keypad, touchpad, keyboard, mouse, touch panel (or touchscreen), joystick, knob, line select key or another suitable device adapted to receive input from a user, such as a microphone, audio transducer, audio sensor, or another audio input device.

The control module 1502 generally represents the hardware, circuitry, logic, firmware and/or other component of the medical device 1500 configured to determine dosage commands for operating medical device 1500 (e.g., by operating an actuation arrangement to deliver fluid to the body of a patient) and perform various additional tasks, operations, functions and/or operations described herein. For example, in exemplary embodiments, control module 1502 implements or otherwise executes an application that supports establishing communications sessions with a guidance application on an auxiliary device and automatically pushing or uploading status information, settings information, and the like to the guidance application asynchronously or in another substantially real-time manner. Depending on the embodiment, the control module 1502 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 1502, or in any practical combination thereof. In exemplary embodiments, the control module 1502 includes or otherwise accesses the data storage element or memory 1510, which may be realized using any sort of non-transitory computer-readable medium capable of storing programming instructions for execution by the control module 1502. The computer-executable programming instructions, when read and executed by the control module 1502, cause the control module 1502 to implement or otherwise generate the guidance communications application and perform tasks, operations, functions, and processes described herein.

In exemplary embodiments described herein, the memory 1510 may also store or otherwise maintain settings information for the medical device 1500 including, but not limited to, data indicating which modes or features of the medical device 1500 have been configured, data indicating which modes or features of the medical device 1500 have not been configured, data indicating which modes or features of the medical device 1500 are enabled or activated, data indicating which modes or features of the medical device 1500 have been disabled or deactivated, variables, parameters, or other values that have been programmed, configured, entered, or otherwise established for use by a particular mode or feature of the medical device 1500, and any patient-specific variables, parameters, or other values that have been programmed, configured, entered or otherwise established for use by a particular mode or feature of the medical device 1500. In this regard, the settings information may include configuration data for an operating mode of the medical device 1500, configuration data for a feature of the medical device 1500, or values or data for other patient-specific settings, parameters, or variables. For example, for an infusion device, the settings information could include a value for a basal rate, a patient-specific insulin sensitivity factor, a patient-specific insulin-to-carbohydrate ratio, a patient-specific total daily insulin requirement, or the like.

As described above in the context of FIGS. 2-10, in exemplary embodiments, in response to establishing a communications session with an auxiliary device via the communications interface 1504, the control module 1502 (or the guidance communications application executing thereon) is configured to identify or otherwise obtain status information characterizing the current state of the display device 1506 and the user interface 1508 and the settings information stored by the memory 1510 and transmit the settings information and the status information to the auxiliary device via the communications session. Thereafter, in response to receiving a user input via the user interface 1508, the control module 1502 automatically identifies or obtains updated status information characterizing the updated state of the display device 1506 and the user interface 1508 responsive to the user input and automatically pushes, uploads, or otherwise transmits the updated status information to the auxiliary device, which, in turn, allows the auxiliary device to dynamically update any guidance information presented to a user at the auxiliary device. For example, as described above, the guidance information may include a sequence of one or more user actions with respect to the user interface 1508 for operating the medical device 1500 to deliver a bolus of fluid, configuring or enabling an operating mode or feature of the medical device 1500 (e.g., a closed-loop operating mode, a bolus wizard feature, or the like), programming patient-specific variables, parameters, or other settings into the medical device 1500, and/or the like, with the sequence of user actions being dynamically updated to reflect or distinguish those user actions that have already been performed.

For the sake of brevity, conventional techniques related to glucose sensing and/or monitoring, glucose regulation, communications networks, sessions, and security, graphical user interfaces, menus and navigation thereof, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

We claim:

1. A system comprising:
   one or more processors; and
   one or more processor-readable media storing instructions which, when executed by the one or more processors, cause performance of:
      identifying, by an application executing on a computing device, a user objective with respect to a medical device communicatively coupled to the computing device, the medical device having a graphical user interface,
      obtaining, by the application, state information indicative of a current display of the graphical user interface of the medical device,
      generating, by the application based on the current display of the graphical user interface, a guidance user interface indicative of user actions for achieving the user objective, the guidance user interface comprising an ordered sequence of actuations of user input elements of the medical device to navigate to a screen of the graphical user interface to achieve the identified user objective, wherein the ordered sequence of actuations identifies a first button on the medical device, a number of times that the first button should be actuated during the ordered sequence of actuations, a second button on the medical device, wherein the second button is different from the first button, and a number of times that the second button should be actuated during the ordered sequence of actuations,
      responsive to an actuation of a user input element of the ordered sequence of actuations of user input elements, obtaining, by the application, updated state information for an updated state of the graphical user interface of the medical device, and
      dynamically updating, by the application, the guidance user interface based on the updated state information.

2. The system of claim 1, wherein the one or more processor-readable media further store instructions which, when executed by the one or more processors, cause performance of:
   obtaining, by the application, settings information corresponding to a current configuration of the medical device.

3. The system of claim 2, wherein the guidance user interface is generated based on the settings information.

4. The system of claim 2, wherein the settings information corresponds to a feature of the medical device, and wherein the user objective is to enable the feature.

5. The system of claim 4, wherein the feature corresponds to a fluid delivery feature of the medical device.

6. The system of claim 1, wherein the graphical user interface comprises a menu.

7. The system of claim 6, wherein the state information is indicative of user selection of an item on the menu.

8. The system of claim 1, wherein the guidance user interface comprises explanatory information.

9. A processor-implemented method comprising:
   identifying, by an application executing on a computing device, a user objective with respect to a medical device communicatively coupled to the computing device, the medical device having a graphical user interface;
   obtaining, by the application, state information indicative of a current display of the graphical user interface of the medical device;
   generating, by the application based on the current display of the graphical user interface, a guidance user interface comprising an ordered sequence of actuations of user input elements of the medical device to navigate to a screen of the graphical user interface to achieve the identified user objective, wherein the ordered sequence of actuations identifies a first button on the medical device, a number of times that the first button should be actuated during the ordered sequence of actuations, a second button of the medical device, wherein the second button is different from the first button, and a number of times that the second button should be actuated during the ordered sequence of actuations;
   responsive to an actuation of a user input element of the ordered sequence of actuations of user input elements, obtaining, by the application, updated state information for an updated state of the graphical user interface of the medical device; and
   dynamically updating, by the application, the guidance user interface based on the updated state information.

10. The method of claim 9, further comprising:
   obtaining, by the application, settings information corresponding to a current configuration of the medical device.

11. The method of claim 10, wherein the guidance user interface is generated based on the settings information.

12. The method of claim 10, wherein the settings information corresponds to a feature of the medical device, and wherein the user objective is to enable the feature.

13. The method of claim 12, wherein the feature corresponds to a fluid delivery feature of the medical device.

14. The method of claim 9, wherein the graphical user interface comprises a menu.

15. The method of claim 14, wherein the state information is indicative of user selection of an item on the menu.

16. The method of claim 9, wherein the guidance user interface comprises explanatory information.

17. One or more non-transitory processor-readable media storing instructions which, when executed by one or more processors, cause performance of:
identifying, by an application executing on a computing device, a user objective with respect to a medical device communicatively coupled to the computing device, the medical device having a graphical user interface;
obtaining, by the application, state information indicative of a current display of the graphical user interface of the medical device;
generating, by the application based on the current display of the graphical user interface, a guidance user interface comprising an ordered sequence of actuations of user input elements of the medical device to navigate to a screen of the graphical user interface to achieve the identified user objective, wherein the ordered sequence of actuations identifies a first button on the medical device, a number of times that the first button should be actuated during the ordered sequence of actuations, a second button of the medical device, wherein the second button is different from the first button, and a number of times that the second button should be actuated during the ordered sequence of actuations;
responsive to an actuation of a user input element of the ordered sequence of actuations of user input elements, obtaining, by the application, updated state information for an updated state of the graphical user interface of the medical device; and
dynamically updating, by the application, the guidance user interface based on the updated state information.

18. The one or more non-transitory processor-readable media of claim 17, further storing instructions which, when executed by the one or more processors, cause performance of:
obtaining, by the application, settings information corresponding to a current configuration of the medical device.

19. The one or more non-transitory processor-readable media of claim 18, wherein the guidance user interface is generated based on the settings information.

20. The one or more non-transitory processor-readable media of claim 18, wherein the settings information corresponds to a feature of the medical device, and wherein the user objective is to enable the feature.

* * * * *